(12) United States Patent
Kim

(10) Patent No.: US 6,815,180 B1
(45) Date of Patent: Nov. 9, 2004

(54) HUMAN CERVICAL CANCER 1 PROTOONCOGENE AND PROTEIN ENCODED THEREIN

(76) Inventor: Jin-Woo Kim, Hyundai Apt. 118-804,Apkujung-dong, Kangnam-ku, Seoul (KR), 135-110

( * ) Notice: Subject to any disclaimer, the term of this patent is extended or adjusted under 35 U.S.C. 154(b) by 0 days.

(21) Appl. No.: 09/868,474

(22) PCT Filed: Mar. 30, 2000

(86) PCT No.: PCT/KR00/00284

§ 371 (c)(1),
(2), (4) Date: Jun. 15, 2001

(87) PCT Pub. No.: WO01/27149

PCT Pub. Date: Apr. 19, 2001

(30) Foreign Application Priority Data

Oct. 15, 1999 (KR) ........................................ 1999-44811

(51) Int. Cl.⁷ ........................ C07H 21/04; C12N 15/00
(52) U.S. Cl. ...................... 435/69.1; 435/6; 435/320.1; 435/325; 435/243; 435/252.1; 435/252.3; 435/252.33; 536/23.1; 536/24.1; 536/24.5
(58) Field of Search ............................... 536/23.1, 24.1, 536/24.5; 435/69.1, 6, 320.1, 325, 249, 252.1, 252.3, 252.33

(56) References Cited

PUBLICATIONS

New England Biolabs Catalog, pp. 106–108, 1995.*
Jen et al., Stem Cell, vol. 18:307–319, 2000.*
Branch A., TIBS, vol. 23:45–.*
Agrawal, S., TIBTECH, vol. 14:376–387, 1996.*

* cited by examiner

Primary Examiner—Sean McGarry
(74) Attorney, Agent, or Firm—Anderson Kill & Olick, PC

(57) ABSTRACT

A human cervical cancer 1 protooncogene having a base sequence of SEQ ID:1 or a fragment thereof is overexpressed in various cancer tissues and can be used in diagnosing various cancers and an anti-sense gene complementary thereto can be used in treating cancers.

15 Claims, 21 Drawing Sheets

35 kDa →

← 198 bp

← 497 bp

SEQUENCE LISTING

```
<160> NUMBER OF SEQ ID NOS: 7

<210> SEQ ID NO 1
<211> LENGTH: 2118
<212> TYPE: DNA
<213> ORGANISM: Homo sapiens
<220> FEATURE:
<221> NAME/KEY: CDS
<222> LOCATION: (9)..(1088)
<221> NAME/KEY: sig_peptide
<222> LOCATION: (9)..(83)
<221> NAME/KEY: misc_feature
<222> LOCATION: (435)..(494)
<223> OTHER INFORMATION: transmembrane domain

<400> SEQUENCE: 1 ctgtgaag atg gcg ctc tcc agg gtg tgc tgg gct cgg tcg gct gtg tgg      50
```

```
            Met Ala Leu Ser Arg Val Cys Trp Ala Arg Ser Ala Val Trp
            1               5                   10 ggc tcg gca gtc acc cct gga cat ttt gtc acc cgg agg ctg caa ctt      98
Gly Ser Ala Val Thr Pro Gly His Phe Val Thr Arg Arg Leu Gln Leu
15              20                  25                  30 ggt cgc tct ggc ctg gct tgg ggg gcc cct cgg tct tca aag ctt cac     146
Gly Arg Ser Gly Leu Ala Trp Gly Ala Pro Arg Ser Ser Lys Leu His
                35                  40                  45 ctt tct cca aag gca gat gtg aag aac ttg atg tct tat gtg gta acc     194
Leu Ser Pro Lys Ala Asp Val Lys Asn Leu Met Ser Tyr Val Val Thr
            50                  55                  60 aag aca aaa gcg att aat ggg aaa tac cat cgt ttc ttg ggt cgt cat     242
Lys Thr Lys Ala Ile Asn Gly Lys Tyr His Arg Phe Leu Gly Arg His
        65                  70                  75 ttc ccc cgc ttc tat atc ctg tac aca atc ttc atg aaa gga ttg cag     290
Phe Pro Arg Phe Tyr Ile Leu Tyr Thr Ile Phe Met Lys Gly Leu Gln
    80                  85                  90 atg tta tgg gct gat gcc aaa aag gct aga aga ata aag aca aat atg     338
Met Leu Trp Ala Asp Ala Lys Lys Ala Arg Arg Ile Lys Thr Asn Met
95                  100                 105                 110 tgg aag cac aat ata aag ttt cat caa ctt cca tac cgg gag atg gag     386
Trp Lys His Asn Ile Lys Phe His Gln Leu Pro Tyr Arg Glu Met Glu
                115                 120                 125 cat ttg aga cag ttc cgc caa gac gtc acc aag tgt ctt ttc cta ggt     434
His Leu Arg Gln Phe Arg Gln Asp Val Thr Lys Cys Leu Phe Leu Gly
            130                 135                 140 att att tcc att cca cct ttt gcc aac tac ctg gtc ttc ttg cta atg     482
Ile Ile Ser Ile Pro Pro Phe Ala Asn Tyr Leu Val Phe Leu Leu Met
        145                 150                 155 tac ctg ttt ccc agg caa cta ctg atc agg cat ttc tgg acc cca aaa     530
Tyr Leu Phe Pro Arg Gln Leu Leu Ile Arg His Phe Trp Thr Pro Lys
    160                 165                 170 caa caa act gat ttc tta gat atc tat cat gct ttc cgg aag cag tcc     578
Gln Gln Thr Asp Phe Leu Asp Ile Tyr His Ala Phe Arg Lys Gln Ser
175                 180                 185                 190 cac cca gaa att att agt tat tta gaa aag gtc atc cct ctc att tct     626
His Pro Glu Ile Ile Ser Tyr Leu Glu Lys Val Ile Pro Leu Ile Ser
                195                 200                 205 gat gca gga ctc cgg tgg cgt ctg aca gat ctg tgc acc aag ata cag     674
Asp Ala Gly Leu Arg Trp Arg Leu Thr Asp Leu Cys Thr Lys Ile Gln
            210                 215                 220 cgt ggt acc cac cca gca ata cat gat atc ttg gct ctg aga gag tgt     722
Arg Gly Thr His Pro Ala Ile His Asp Ile Leu Ala Leu Arg Glu Cys
        225                 230                 235 ttc tct aac cat cct ctg ggc atg aac caa ctc cag gct ttg cac gtg     770
Phe Ser Asn His Pro Leu Gly Met Asn Gln Leu Gln Ala Leu His Val
    240                 245                 250 aaa gcc ttg agc cgg gcc atg ctt ctc aca tct tac ctg cct cct ccc     818
Lys Ala Leu Ser Arg Ala Met Leu Leu Thr Ser Tyr Leu Pro Pro Pro
255                 260                 265                 270 ttg ttg aga cat cgt ttg aag act cat aca act gtg att cac caa ctg     866
Leu Leu Arg His Arg Leu Lys Thr His Thr Thr Val Ile His Gln Leu
                275                 280                 285 gac aag gct ttg gca aag ctg ggg att ggc cag ctg act gct cag gaa     914
Asp Lys Ala Leu Ala Lys Leu Gly Ile Gly Gln Leu Thr Ala Gln Glu
            290                 295                 300 gta aaa tcg gct tgt tat ctc cgt ggc ctg aat tct acg cat att ggt     962
Val Lys Ser Ala Cys Tyr Leu Arg Gly Leu Asn Ser Thr His Ile Gly
        305                 310                 315
```

```
gaa gat agg tgt cga act tgg ctg gga gaa tgg ctg cag att tcc tgc      1010
Glu Asp Arg Cys Arg Thr Trp Leu Gly Glu Trp Leu Gln Ile Ser Cys
        320                 325                 330 agc ctg aaa gaa gct gag ctg tct ctc ttg ctg cac aac gtg gtc ctg      1058
Ser Leu Lys Glu Ala Glu Leu Ser Leu Leu Leu His Asn Val Val Leu
335                 340                 345                 350 ctc tcc acc aac tac ctt ggg aca agg cgc tgaatgaacc atggagcgga        1108
Leu Ser Thr Asn Tyr Leu Gly Thr Arg Arg
                355                 360 tggcattgtc ctgcagtcgt atagtatagc agtgcaggaa caaacagcac ttgccagcaa    1168
agtctgtgtg tactgttaag tgtgtgggag cagagagag  gagcagggc catgggcttc     1228 acagcatggc acacctgtgg gaactgcaga cattcctctc acagctagaa ctgaaacaaa    1288
ccctcttgct agggtggtc cgtgtgaggt gtcatcctgt cccctcata attactaata      1348 gctggaactg gcagcagcct ctactgggct tttactgtga tgtgttcagt tcatgtccta    1408
ggaagtcagc ttttgcccca ggtgggaatc cttatttggc ttaggactga tccacttcca    1468
tgttacttac atctgtgggt ttttgttgtt gctgttagaa aatttttggc tggtgaaaac    1528
agcactcctt tggctggagc acttgtgtcc atgcatgtac ttgggtgttt ccctccatcc    1588
tttctgatat gaccaaaaat caagttgttt tgtttttgt caccttcact ggcatgggct     1648
aaccacttct ttttcaaacc ctctgaacac cttttttctga tgggtaactt gcaggaatat   1708
tctattggaa aagataacag gaagtacaag tgcttcttga ccccttcctc aatgtttcta    1768
gccttcactc tccattgtct tttctgggct gtattacagc cctctgtgga tcttcaactc    1828
tgctgcctcc actgtgatgc agcagtccaa ctgtaactga cagtggctgc cttctctggg    1888
ccatggatca cacctgtaag gtactaatta ctgcccagcc tggggagatc aggagaggtc    1948
tgcatagtta gtaagttggg tttagctttt gtgtgtgcat cagtgactta gagttctgta    2008
ataacttatt gtaaatgcat gaagcactgt ttttaaaccc aagtaaagac tgcttgaaac    2068
ctgttgatgg aaaaaaaaaa aaaaaaaaaa aaaaaaaaaa aaaaaaaaa                2118

<210> SEQ ID NO 2
<211> LENGTH: 360
<212> TYPE: PRT
<213> ORGANISM: Homo sapiens
<220> FEATURE:
<221> NAME/KEY: misc_feature
<222> LOCATION: (435)..(494)
<223> OTHER INFORMATION: transmembrane domain

<400> SEQUENCE: 2

Met Ala Leu Ser Arg Val Cys Trp Ala Arg Ser Ala Val Trp Gly Ser
1               5                   10                  15

Ala Val Thr Pro Gly His Phe Val Thr Arg Arg Leu Gln Leu Gly Arg
            20                  25                  30

Ser Gly Leu Ala Trp Gly Ala Pro Arg Ser Ser Lys Leu His Leu Ser
        35                  40                  45

Pro Lys Ala Asp Val Lys Asn Leu Met Ser Tyr Val Val Thr Lys Thr
    50                  55                  60

Lys Ala Ile Asn Gly Lys Tyr His Arg Phe Leu Gly Arg His Phe Pro
65                  70                  75                  80

Arg Phe Tyr Ile Leu Tyr Thr Ile Phe Met Lys Gly Leu Gln Met Leu
                85                  90                  95

Trp Ala Asp Ala Lys Lys Ala Arg Arg Ile Lys Thr Asn Met Trp Lys
            100                 105                 110
```

-continued

```
His Asn Ile Lys Phe His Gln Leu Pro Tyr Arg Glu Met Glu His Leu
        115                 120                 125

Arg Gln Phe Arg Gln Asp Val Thr Lys Cys Leu Phe Leu Gly Ile Ile
    130                 135                 140

Ser Ile Pro Pro Phe Ala Asn Tyr Leu Val Phe Leu Leu Met Tyr Leu
145                 150                 155                 160

Phe Pro Arg Gln Leu Leu Ile Arg His Phe Trp Thr Pro Lys Gln Gln
                165                 170                 175

Thr Asp Phe Leu Asp Ile Tyr His Ala Phe Arg Lys Gln Ser His Pro
            180                 185                 190

Glu Ile Ile Ser Tyr Leu Glu Lys Val Ile Pro Leu Ile Ser Asp Ala
        195                 200                 205

Gly Leu Arg Trp Arg Leu Thr Asp Leu Cys Thr Lys Ile Gln Arg Gly
    210                 215                 220

Thr His Pro Ala Ile His Asp Ile Leu Ala Leu Arg Glu Cys Phe Ser
225                 230                 235                 240

Asn His Pro Leu Gly Met Asn Gln Leu Gln Ala Leu His Val Lys Ala
                245                 250                 255

Leu Ser Arg Ala Met Leu Leu Thr Ser Tyr Leu Pro Pro Pro Leu Leu
            260                 265                 270

Arg His Arg Leu Lys Thr His Thr Thr Val Ile His Gln Leu Asp Lys
        275                 280                 285

Ala Leu Ala Lys Leu Gly Ile Gly Gln Leu Thr Ala Gln Glu Val Lys
    290                 295                 300

Ser Ala Cys Tyr Leu Arg Gly Leu Asn Ser Thr His Ile Gly Glu Asp
305                 310                 315                 320

Arg Cys Arg Thr Trp Leu Gly Glu Trp Leu Gln Ile Ser Cys Ser Leu
                325                 330                 335

Lys Glu Ala Glu Leu Ser Leu Leu Leu His Asn Val Val Leu Leu Ser
            340                 345                 350

Thr Asn Tyr Leu Gly Thr Arg Arg
        355                 360

<210> SEQ ID NO 3
<211> LENGTH: 18
<212> TYPE: DNA
<213> ORGANISM: Artificial Sequence
<220> FEATURE:
<223> OTHER INFORMATION: anti-sense DNA

<400> SEQUENCE: 3
cctggacatt ttgtcacc                                                   18

<210> SEQ ID NO 4
<211> LENGTH: 18
<212> TYPE: DNA
<213> ORGANISM: Artificial Sequence
<220> FEATURE:
<223> OTHER INFORMATION: sense DNA

<400> SEQUENCE: 4
ggtgacaaaa tgtccagg                                                   18

<210> SEQ ID NO 5
<211> LENGTH: 18
<212> TYPE: DNA
<213> ORGANISM: Artificial Sequence
<220> FEATURE:
<223> OTHER INFORMATION: missense DNA
```

```
<400> SEQUENCE: 5
cgcggatatt tcctcacc                                                    18

<210> SEQ ID NO 6
<211> LENGTH: 20
<212> TYPE: DNA
<213> ORGANISM: Artificial Sequence
<220> FEATURE:
<223> OTHER INFORMATION: forward primer

<400> SEQUENCE: 6
gggagatgga gcatttgaga                                                  20

<210> SEQ ID NO 7
<211> LENGTH: 20
<212> TYPE: DNA
<213> ORGANISM: Artificial Sequence
<220> FEATURE:
<223> OTHER INFORMATION: reverse primer

<400> SEQUENCE: 7
gcttccggaa agcatgatag                                                  20
```

HUMAN CERVICAL CANCER 1 PROTOONCOGENE AND PROTEIN ENCODED THEREIN

CROSS REFERENCE TO RELATED APPLICATION

This application is a continuation patent application of PCT Patent Application No. PCT/KR00/00284, which was filed on March 30, 2000, designating the United States of America.

FIELD OF THE INVENTION

The present invention relates to a novel protooncogene and protein encoded therein, and more particularly, to a human cervical cancer 1 protooncogene and a protein derived therefrom, which can be used in diagnosis of various cancers.

BACKGROUND OF THE INVENTION

Higher animals including man each carry approximately 100,000 genes, but only about 15% thereof is expressed, and characteristics of individual's biological process, e.g., genesis, differentiation, homeostasis, responses to stimuli, control of cell segmentation, aging and apoptosis (programmed cell death), are determined depending on which genes are expressed(see Liang, P. and A. B. Pardee, Science, 257: 967–25 971(1992)).

Pathogenic phenomena such as tumorigenesis are caused by gene mutation which brings about changes in the mode of gene expression. Therefore, comparative studies of gene expressions in various cells have been conducted to provide bases for establishing viable approaches to the understanding of diverse biological phenomena.

For example, the MRNA differential display(DD) method suggested by Liang and Pardee is effective in elucidating the nature of tumor suppressor genes, cell cycle-related genes and transcriptional regulatory genes that control apoptosis (see Liang, P. and A. B. Pardee supra). Further, the DD method has been widely used in examining the interrelationship of various genes in a cell.

It has been reported that tumorigenesis is caused by various genetic changes such as the loss of chromosomal heterozygosity, activation of oncogenes and inactivation of tumor suppressor genes, e.g., p53 gene(see Bishop, J. M., Cell, 64: 235–248(1991); and Hunter, T., Cell, 64: 249–270 (1991)). Further, it has been reported that 10 to 30% of human cancer arises from the activation of oncogene through amplification of protooncogenes.

Therefore, the activation of protooncogenes plays an important role in the etiology of many tumors and there has existed a need to identify protooncogenes.

The present inventor has endeavored to unravel examine the mechanism involved in the tumorigenesis of cervical cancer; and, has unexpectedly found that a novel protooncogene, human cervical cancer 1(HCCR-1), is specifically overexpressed in cancer cells. This protooncogene can be effectively used in diagnosis, prevention and treatment of various cancers, e.g., leukemia, lymphoma, kidney, liver, lung, ovary and uterine cervix cancers.

SUMMARY OF THE INVENTION

Accordingly, the primary object of the present invention is to provide a novel protoncogene and a fragment thereof.

Other objects of the present invention are to provide:

a recombinant vector containing said protooncogene or a fragment thereof and a microorganism transformed therewith;

a protein encoded in said protooncogene and a fragment thereof;

a kit for diagnosis of cancer containing said protooncogene or a fragment thereof;

a kit for diagnosis of cancer containing said protein or a fragment thereof;

an anti-sense gene having a base sequence complementary to that of said protooncogene or a fragment thereof; and a process for treating or preventing cancer by using said anti-sense gene.

In accordance with one aspect of the present invention, there is provided a novel protooncogene having the nucleotide sequence of SEQ ID No:1 or a fragment thereof.

In accordance with another aspect of the present invention, there is provided a recombinant vector containing said protooncogene or a fragment thereof and a microorganism transformed with said vector.

In accordance with still another aspect of the present invention, there is provided a protein having the amino acid sequence of SEQ ID No:2 or a fragment thereof derived from said protooncogene or a fragment thereof

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

The novel protooncogene of the present invention, i.e., human cervical cancer 1(hereinafter "HCCR-1 protooncogene"), consists of 2118 base pairs and has the DNA sequence of SEQ ID NO:1.

In SEQ ID NO: 1, the full open reading frame corresponding to base Nos. 9 to 1088 is a protein encoding region and the predicted amino acid sequence derived therefrom is shown in SEQ ID NO: 2 which consists of 360 amino acids("HCCR-1 protein"). Further, the region corresponding to base Nos. 9 to 83 of SEQ ID NO: 1 encodes a signal peptide with the predicted amino acid sequence of amino acid Nos. 1 to 25 in SEQ ID NO: 2; and the region represented by nucleotide No. 435 to 494 of SEQ ID NO: 1 encodes a single transmembrane domain having the predicted amino acid sequence of amino acid Nos. 143 to 162 of SEQ ID NO: 2. This suggests that the protooncogene of the present invention is a membrane-bound gene.

A single potential N-glycosylation site(corresponding to base Nos. 945 to 953 of SEQ ID NO: 1 and amino acid Nos. 313 to 315 of SEQ ID NO: 2) is present at the C-terminal side of the HCCR-1 protein, which suggests that HCCR-1 is a type II membrane protein. The polyadenylation signal corresponds to the nucleotide Nos. 2008–2012 of SEQ ID NO:1.

Figure 2:
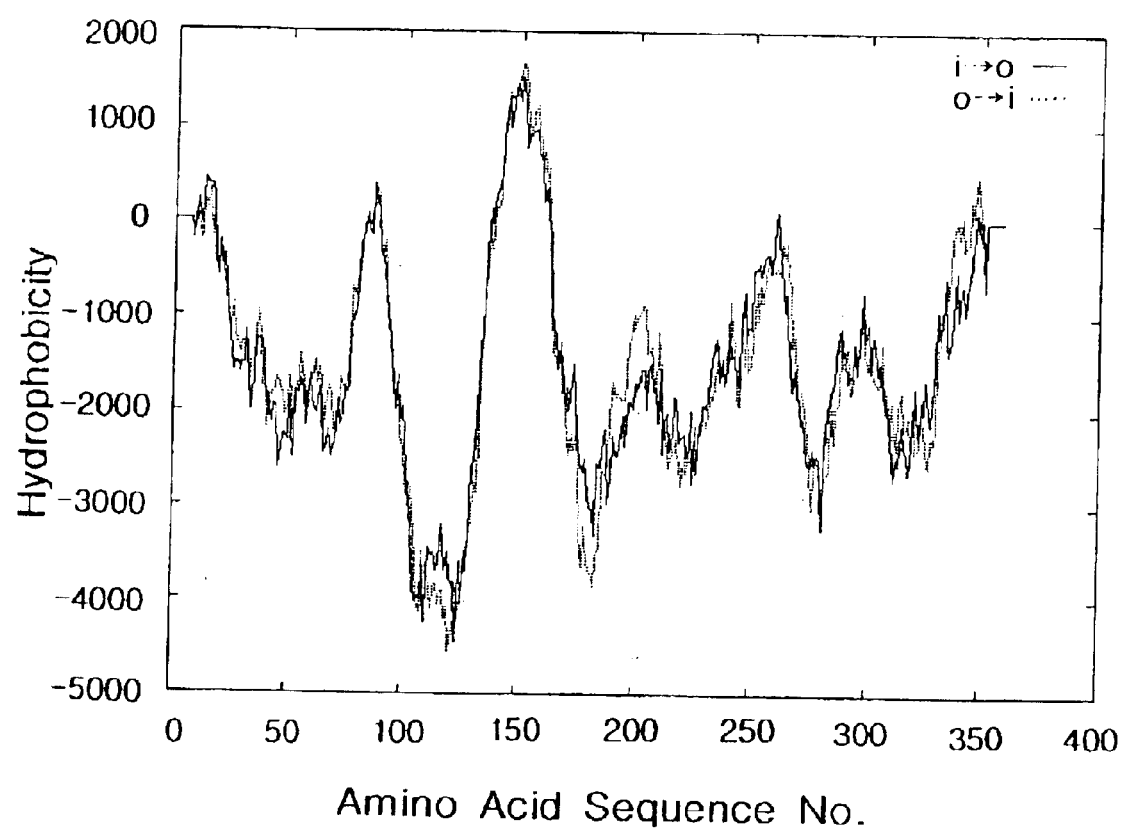
FIG. 2: the prediction of the hydrophobicity of transmembrane regions in the protooncogene of the present invention using TMPRED program.

The predicted extracellular domain of HCCR-1 corresponds to base Nos. 495–1088 with the predicted amino acid sequence of amino acid Nos. 163–360 consisting of 198 amino acids with 5 cysteine residues. The predicted intracellular domain contains 117 amino acids(corresponding to nucleotide Nos. 84–434 of SEQ ID NO:1 and amino acid Nos. 26–142 of SEQ ID NO:2) with two potential protein kinase C(PKC) phosphorylation sites at Ser42 and Ser-48, and two potential N-myristylation sites at Gly-34 and Gly-38. Further computer-assisted analyses indicate that HCCR-1 is markedly hydrophobic and possesses a characteristic single membrane-spanning domain and pre-secretory signal peptide as shown in FIG. 2.

In consideration of the degeneracies of codons and the preferred codons in a specific animal wherein the protooncogene of the present invention is to be expressed, various changes and modifications of the DNA sequences of SEQ ID NO:1 may be made, e.g., in the coding area thereof without adversely altering the amino acid sequence of the expressed protein, or in the non-coding area without adversely affecting the expression of the protooncogene. Therefore, the present invention also includes, in its scope, a polynucleotide having substantially the same base sequence as the inventive protooncogene, and a fragment thereof. As used herein, "substantially the same polynucleotide" refers to a polynuleotide whose base sequence shows 80% or more, preferably 90% or more, most preferably 95% or more homology to the protooncogene of the present invention.

The protein expressed from the protooncogene of the present invention consists of 360 amino acids and has the amino acid sequence of SEQ ID NO: 2. The molecular weight of this protein is about 40 kDa. However, various substitution, addition and/or deletion of the amino acid residues of protein may be performed without adversely affecting the protein's function. Further, a portion of the protein may be used when a specific purpose is to be fulfilled. These modified amino acids and fragments thereof are also included in the scope of the present invention. Therefore, the present invention includes, in its scope, a polypeptide having substantially the same amino acid sequence as the protein derived from the oncogene of the present invention and a fragment thereof. As used herein, "substantially the same polypeptide" refers to a polypeptide whose amino acid sequence shows 80% or more, preferably 90% or more, most preferably 95% or more homology to the amino acid sequence of SEQ ID NO:2.

The protooncogene, or the protein, of the present invention can be obtained from human cancer tissues or synthesized using a conventional DNA or peptide synthesis method. Further, the gene thus prepared may be inserted to a conventional vector to obtain an expression vector, which may, in turn, be introduced into a suitable host, e.g., an *E. coli* or yeast cell, The cells transformed with a vector containing the HCCR-1 protooncogene or a fragment thereof is hereinafter referred to a "HCCR-1 cell".

The transformed host may then be used in producing the inventive DNA or protein on a large scale. For example, *E. coli* JM109 is transfected with HCCR- 1 protooncogene by using pGEM-T easy vector and the JM109/HCCR-1 was deposited on Oct. 11, 1999 with the Korean Collection for Type Cultures(KCTC)(Address: Korea Research Institute of Bioscience and Biotechnology(KRIBB), #52, Oun-dong, Yusong-ku, Taejon, 305–333, Republic of Korea) under the accession number, KCTC 0667BP, in accordance with the terms of Budapest Treaty on the International Recognition of the Deposit of Microorganism for the Purpose of Patent Procedure.

In preparing a vector, expression-control sequences, e.g., promoter. terminator, self replication sequence and secretion signal, are suitably selected depending on the host cell used.

The overexpression of the protooncogene of the present invention occurs not in normal cervical and lung tissues but in cervical cancer tissues, cervical cancer cell lines and lung cancer cell lines. This suggests that the protooncogene of the present invention induces cervical and lung cancers. Further, when a normal fibroblast cell, e.g., NIH/3T3 cell line, is transfected with the protooncogene of the present invention, an abnormal cells is produced. Morphological characterizations with optical and electronic microscopes show that the abnormal cell has the form of a tumor cell.

When the normal fibroblast cell transfected with the protooncogene of the present invention is injected into the posterial lateral aspect of a nude mouse, tumorigenesis is observed after about 21 days from the injection, the tumor size becoming 1.5 cm×1.5 cm in 40 days. By using hematoxylineosin dye method, it can be confirmed that the tumor cells are cancerous. The formation of the epithelial carcinoma can also be confirmed by using transmission electron microscopy and immunhistochemical staining methods.

In addition to epithelial tissues such as cervical and lung cancer tissues, the overexpression of the protooncogene of the present invention is also observed in various other cancer tumors such as leukemia, lymphoma, kidney, liver and ovarian cancers. Therefore, the protooncogene of the present invention is believed to be a factor common to all forms of various cancer and it can be advantageously used in the diagnosis of various cancers and the production of a transformed animal as well as in an anti-sense gene therapy.

A diagnostic method that can be performed using the protooncogene of the present invention may comprise, for example, the steps of hybridizing nucleic acids separated from the body fluid of a subject with a probe containing the protooncogene of the present invention or a fragment thereof, and determining whether the subject has the protooncogene by using a conventional detection method in the art. The presence of the protooncogene may be easily detected by labeling the probe with a radioisotope or an enzyme. Therefore, a cancer diagnostic kit containing the protooncogene of the present invention or a fragment thereof is also included in the scope of the present invention.

A transformed animal produced by introducing the protooncogene of the present invention into a mammal, e.g., a rat, is also included in the scope of the present invention. In producing such a transformed animal, it is preferred to introduce the inventive protooncogene to a fertilized egg of an animal before the 8th cell cycle stage. The transformed animal can be advantageously used in screening for carcinogens or anticancer agents such as antioxidants.

The present invention also provides an anti-sense gene which is useful in a gene therapy. As used herein, the term "an anti-sense gene" means a polynucleotide comprising a base sequence which is fully or partially complementary to the sequence of the mRNA which is transcribed from the protooncogene having the base sequence of SEQ ID NO:1 or a fragment thereof, said nucleotide being capable of preventing the expression of the open reading frame(ORF) of the protooncogene by way of attaching itself to the protein-binding site of mRNA.

An example of the anti-sense gene of the present invention is a 18-mer HCCR-1 anti-sense oligodeoxinucleotide (ODN) having the base sequence of SEQ ID NO:3. Therefore, the present invention also includes, in its scope, a polynucleotide comprising substantially the same base sequence as SEQ ID NO:3 and a fragment thereof.

The present invention also includes within its scope a process for treating or preventing cancer in a subject by way of administering a therapeutically effective amount of the inventive anti-sense gene thereto.

In the inventive anti-sense gene therapy, the anti-sense gene of the present invention is administered to a subject in a conventional manner to prevent the expression of the protooncogene. For example, the anti-sense ODN is mixed with a hydrophobized poly-L-lysine derivative by electrostatic interaction in accordance with the method disclosed by Kim, J. S. et al.(*J. Controlled Release*, 53, 175–182(1998)) and the resulting mixed anti-sense ODN is administered intravenously to a subject.

The present invention also includes within its scope an anti-cancer composition comprising the anti-sense gene of the present invention as an active ingredient, in association with pharmaceutically acceptable carriers, excipients or other additives, if necessary. The pharmaceutical composition of the present invention is preferably formulated for administration by injection.

The amount of the anti-sense gene actually administered should be determined in light of various relevant factors including the condition to be treated, the chosen route of administration, the age and weight of the individual patient, and the severity of the patient's symptoms.

The protein expressed from the inventive protooncogene may be used in producing an antibody useful as a diagnostic tool. The antibody of the present invention may be prepared in the form of a monoclonal or polyclonal antibody in accordance with any of the methods well known in the art by using a protein having the amino acid sequence of SEQ ID NO:2 or a fragment thereof. Cancer diagnosis may be carried out using any of the methods known in the art, e.g., enzyme linked immunosorbentassay(ELISA), radioimmunoassay(RIA), sandwich assay, western blot or immunoassay blot on polyacrylic gel, to asses whether the protein is expressed in the body fluid of the subject. Therefore, a cancer diagnostic kit containing the protein having the amino acid sequence of SEQ ID NO:2 or a fragment thereof is also included in the scope of the present invention.

A continuously viable cancer cell line may be established by using the protooncogene of the present invention, and such a cell line may be obtained, for example, from tumor tissues formed on the back of a nude mouse by injecting fibroblast cells transformed with the protooncogene of the present invention. The cell lines thus prepared may be advantageously used in searching for anti-cancer agents.

The following Examples and Test Examples are given for the purpose of illustration only, and are not intended to limit the scope of the invention.

EXAMPLE 1

Cultivation of Tumor Cells and Separation of Total RNA

Step 1-1: Cultivation of Tumor Cells

For differential display of mRNA, normal cervical tissues, untreated primary cervical cancer tissues and metastatic common iliac lymph node tissues were obtained from cervical cancer patients who underwent radical hysterectomy. The human cervical cancer cell line used in the differential display method was CUMC-6 cell line described by Kim et al.,(*Gynecol. Oncol.*, 62: 230–240(1996)).

Cells from the above-described tissues and CUMC-6 were maintained on Waymouth's MB 752/1 medium (Gibco) supplemented with 2 mmol/L of glutamine, 100 IU/ml of penicillin, 100 µg/ml of streptomycin, and 10% of fetal bovine serum (Gibco). Only the cell suspensions with greater than 95% viability, as assessed by trypan blue dye exclusion described by Freshney("Culture of Animal Cells: A Manual of Basic Technique" 2nd Ed., A. R. Liss, New York(1987)) were used in the present experiments.

Step 1-2: Isolation of Total RNA and Differential Display of mRNA

Total RNAs were extracted from normal cervical tissues, primary cervical cancer tissues, metastatic common iliac lymph node tissues and CUMC-6 cells obtained in Step 1-1 using a commercial system (RNeasy total RNA kit) provided by Qiagen (Qiagen Inc., Germany) and the removal of DNA contaminants from the RNAs was accomplished using Message clean kit (GenHunter Corp., Brookline, Mass.).

EXAMPLE 2

Differential Display Reverse Transcription(DDRT)-PCR

Differential display reverse transcription was performed in accordance with the reverse transcription-polymerase chain reaction (RT-PCR) method described by Liang and Pardee(1992), supra, with minor modifications.

First, reverse transcription was carried out using 0.2 µg each of the total RNAs obtained in Step 1-2 of Example 1 and one of the three primers, i.e., H-TIIG, H-TIIC, or H-TIIA, as anchored oligo-dT primers (RNAimage kit, GenHunter Cor., Mass., USA).

Then PCR was conducted using the same anchored primers and one of the arbitrary 5' 13 mer (RNAimage primer sets 1–4, H-AP 1–32) in the presence of 0.5 mM [$\alpha$-$^{35}$S]-labeled dATP (1200 Ci/mmol). The PCR thermal cycle was repeated 40 times, the cycle being composed of: 95 ° C. for 40 sec., 40° C. for 2 min. and 72 ° C. for 40 sec., and finally the reaction was carried out at 72 ° C. for 5 min.

PCR-amplified fragments were resolved in 6% polyacrylamide sequencing gels. Differentially expressed fragments were identified by inspection of autoradiograms.

Bands of more than 200 base pairs, CC214, were excised from the dried sequencing gel. The CC214 cDNAs were eluted by boiling for 15 min and reamplified with the same primer pairs and PCR conditions as used in the above amplification step except that no [$\alpha$-$^{35}$S]-labeled DATP and 20 µM dNTPs were used.

EXAMPLE 3

Cloning

The reamplified CC214 PCR product obtained as above was inserted into the pGEM-T Easy vector using an TA cloning system (Promega, USA) in accordance with the manufacturer's instructions.

Step 3-1

Ligation

2 µl of the reamplified CC214 PCR product obtained in Example 2, 1 µl of pGEM-T easy vector (50 ng), 1 µl of T4 DNA ligase 10× buffer solution and 1 µl of T4 DNA ligase(3 weiss units/µl; T4 ligase, Promega, USA) were charged into a 0.5 ml tube and distilled water was added thereto to a final volume of 10 µl. The ligation reaction mixture was incubated overnight at 14° C.

Step 3-2: TA Cloning Transformation

TA cloning transformation was performed using the following protocol.

*E. coli* JM109(Promega, WI, USA) was incubated in 10 ml of LB broth(Bacto-trypton 10g, Bacto-yeast extract 5 g, NaCl 5 g) until the optical density at 600 nm reached about 0.3 to 0.6. The cultured mixture was kept at 0° C. for 10 minutes and centrifuged at 4000 rpm at 4° C. for 10 minutes. The supernatant was removed and cells were harvested. The harvested cell pellet was exposed to 10 ml of 0.1 M $CaCl_2$ at 0° C. for 30 minutes to 1 hour to obtain competent cells. The resultant was centrifuged at 4000 rpm at 4° C. for another 10 minutes and the collected cells were suspended in 2 ml of 0.1 M $CaCl_2$ at 0° C.

200 µl of the competent cell suspension was transferred to a microfuge tube and 2 µl of the ligation product obtained in Step 3-1 was added thereto. The mixture was incubated in a water bath at 42° C. for 90 seconds and rapidly cooled to 0° C. Added thereto was 800 µl of SOC medium (Bacto-trypton 2.0 g, Bacto-yeast extract 0.5 g, 1 M NaCl 1 ml, 1 M KCl 0.25 ml, TDW 97 ml, 2M $Mg^{2+}$1 ml, 2M glucose 1 ml) and the mixture was incubated at 37° C. for 45 minutes at 220 rpm in a rotary shaking incubator.

LB agar plates containing ampicillin(50 µl/ml) were prepared by spreading 25µl of X-gal (40 mg/ml stock in dimethylformamide) on top of agar with a glass spreader. 25 µl of the transformed cells thus obtained was spread thereon and the plates were incubated at a 37° C. incubator overnight. White colonies were loaded on an LB agar plate containing ampicillin and transformed *E. coli*, i.e., JM109/CC214 were selected and incubated in a terrific broth(TDW 900 ml, Bacto-trypton 12 g, Bacto-yeast extract 24 g, glycerol 4 ml, 0.17 M $KH_2PO_4$, 0.72 N $K_2HPO_4$ 100 ml).

EXAMPLE 4

Separation of Recombinant Plasmid DNA

The CC214 DNA of the transformed *E. coli* was separated by employing Wizard™ Plus Minipreps DNA Purification Kit(Promega, USA) in accordance with the manufacturer's instructions.

A portion of the plasmid DNA thus separated was treated with ECoRI enzyme and subjected to gel electrophoresis to confirm the insertion of CC214 partial sequence in the plasmid.

EXAMPLE 5

Sequence Analysis of DNA

The CC214 PCR product obtained in Example 2 was subjected to PCR in accordance with the conventional method and the cloned, reamplified CC214 PCR fragments were subjected to sequence analysis is according to the dideoxy chain termination method using a Sequenase version 2.0 DNA sequencing kit (United states Biochemical, Cleveland, Ohio) in accordance with the manufacturer's instructions.

The base sequence of the DNA corresponds to nucleotide Nos. 1883–2088 in SEQ ID NO:1 and is designated "CC214".

Figure 1:
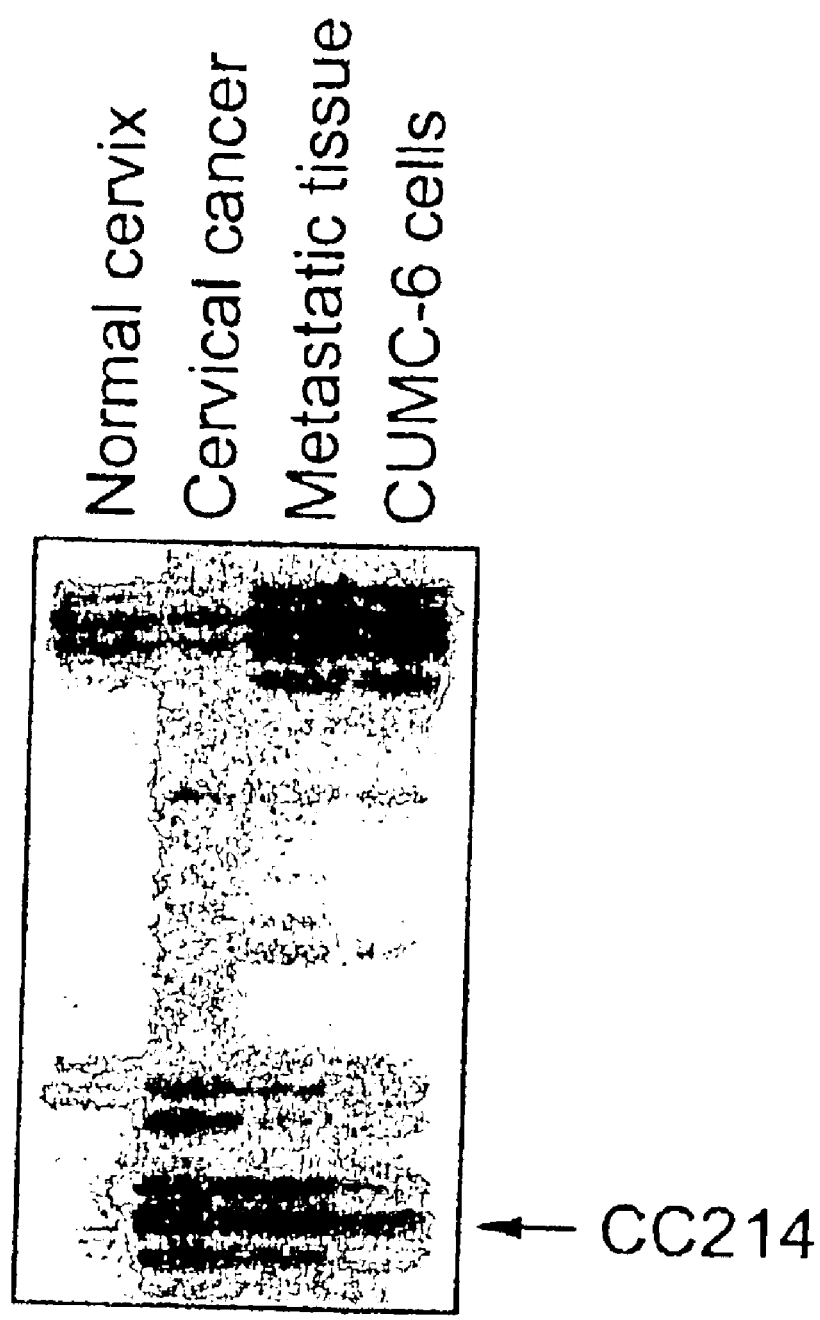
FIG. 1: the DD identification of altered gene expression in normal cervix tissue, primary cervical cancer tissue, metastatic lymph node tissue and CUMC-6 cervical cancer cells.

The differential display reverse transcription polymerase chain reaction(DDRT-PCR) of the 206 bp cDNA fragment, i.e., CC214 obtained above was carried out using a 5' arbitrary primer H-AP21 and a 3' H-TIIC anchored primer and resolved by electrophoresis. Identification of altered gene expression by DD in the primary cervical cancer, metastatic lymph node tissue and CUMC-6 cells is shown in FIG. 1. As can be seen in FIG. 1, the 206 bp cDNA fragment, i.e., CC214 was expressed in the cervical cancer, metastatic tissue and CUMC-6 cervical cancer cells but not in the normal tissue.

EXAMPLE 6

Full Length cDNA Sequence Analysis of the HCCR-1 Protooncogene

A bacteriophage λ gt11 human lung embryonic fibroblast cDNA library (see Miki, T. et al., Gene, 83:137–146(1989)) was screened by plaque hybridization with $^{32}$P-labeled CC214 as a probe. The full-length HCCR-1 cDNA clone, containing a 2118 bp insert in pCEV-LAC. vector was obtained from the human lung embryonic fibroblast cDNA library and registered at GenBank on Nov. 5, 1999 under the accession number AF195651.

HCCR-1 clone inserted into λpCEV vector(see Miki, T. et al., supra) was excised out of the phage in the form of the ampicilline-resistant pCEV-LAC. phagemid vector(see Miki, T. et al., supra) by Not I cleavage.

To make a HCCR-1 plasmid DNA, pCEV-LAC vector containing HCCR-1 gene was ligated with T4 DNA ligase and ligated clone was transformed into *E. coli* JM 109.

The transformed *E. coli* JM109/HCCR1 thus obtained was deposited on Oct. 11, 1999 with the Korean Collection for Type Cultures(KCTC)(Address: Korea Research Institute of Bioscience and Biotechnology(KRIBB), #52, Oun-dong, Yusong-ku, Taejon, 305–333, Republic of Korea) under the accession number, KCTC 0667BP, in accordance with the terms of Budapest Treaty on the International Recognition of the Deposit of Microorganism for the Purpose of Patent Procedure.

The full sequence of HCCR-1 consists of 2118 bp which is identified in SEQ ID NO:1.

In SEQ ID NO:1, the full open reading frame of the HCCR-1 protooncogene of the present invention corresponds to nucleotides No. 9 to 1088 and is predicted to encode amino acid sequence shown in SEQ ID NO:2 which consists of 360 amino acids. Further, the region corresponding to nucleotide Nos. 9 to 83 of SEQ ID NO:1 encodes a signal peptide having amino acids corresponding to amino acid Nos. 1 to 25 of SEQ ID NO:2; the region of nucleotide Nos. 435 to 494 of SEQ ID NO:1 encodes a single transmembrane domain whose amino acid sequence corresponds to amino acid Nos. 143 to 162 in SEQ ID NO:2. This indicates that the protooncogene of the present invention is a membrane-bound gene.

A single potential N-glycosylation site(corresponding to base Nos. 945 to 953 of SEQ ID NO: 1 and amino acid Nos. 313 to 315 of SEQ IS NO: 2) is present at the C-terminal side of the HCCR-1 protein, which suggests that HCCR-1 is a type II membrane protein. The polyadenylation signal corresponds to the nucleotide Nos. 2008–2012 of SEQ ID NO:1.

The predicted extracellular domain contains 198 amino acids with 5 cysteine residues. The predicted intracellular domain contains 117 amino acids(corresponding to nucleotide Nos. 84–434 of SEQ ID NO:1 and amino acid Nos. 26–142 of SEQ ID NO:2) with two potential PKC. phosphorylation sites at Ser-42 and Ser-48, and two potential N-myristylation sites at Gly-34 and Gly-38. Further computer-assisted analyses indicated that HCCR-1 is markedly hydrophobic and possesses a characteristic single membrane-spanning domain and pre-secretory signal peptide as shown in FIG. 2. In FIG. 2, the X-axis represents the amino acid sequence number of the peptide of the present invention and the Y-axis, the hydrophobicity of the peptide.

EXAMPLE 7

Northern Blot Analysis of the HCCR-1 Gene in Various Cells

Total RNAs were extracted from various tissues and cell lines as in Example 1.

To determine the level of HCCR-1 gene expression, 20 μg denatured total RNAs from each tissue or cell lines were electrophoresed through 1% formaldehyde agarose gel and transferred to nylon membranes (Boehringer-Mannheim, Germany). The blots were hybridized with a $^{32}$P-labeled random-primed HCCR-1 full CDNA probe which was prepared using a rediprime II random prime labeling system (Amersham, England). The northern blot analysis was repeated twice and the results were quantified by densitometry and normalized with β-actin.

Figure 3:
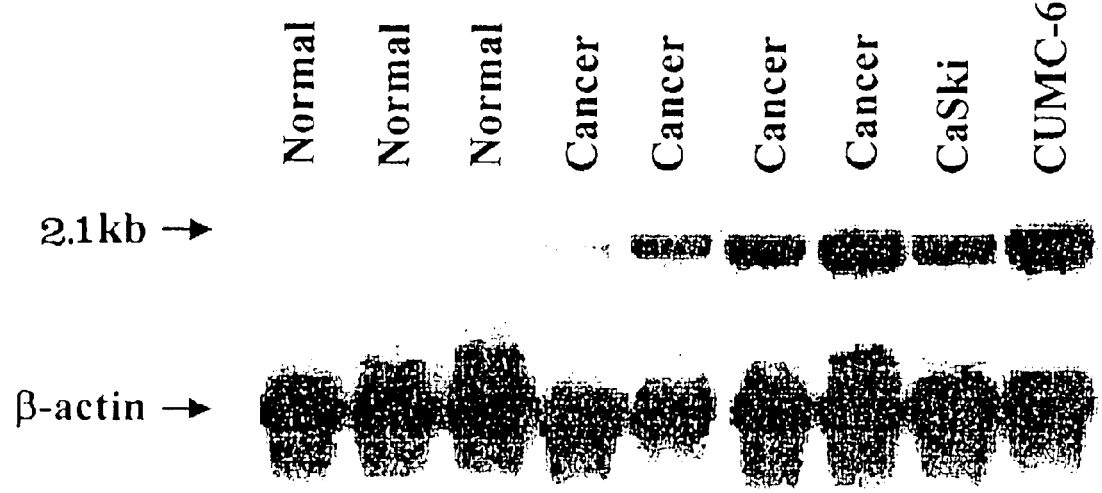
FIG. 3: the results of northern blot analyses for HCCR-1 gene expressed in normal cervical tissues, cervical cancer tissues and cervical cancer cell lines(CaSki and CUMC-6)

FIG. 3 shows the results of northern blot analyses for HCCR-1 gene expressed in normal cervical tissues, cervical cancer tissues and cervical cancer cell lines(CaSki and CUMC-6). As can be seen in FIG. 3, the transcription level of HCCR-1 is high in the cervical cancer tissues and cancer cell lines (CaSki(ATCC CRL 1550) and CUMC-6), but very low or undetactable in the normal cervical tissues.

Figure 4:
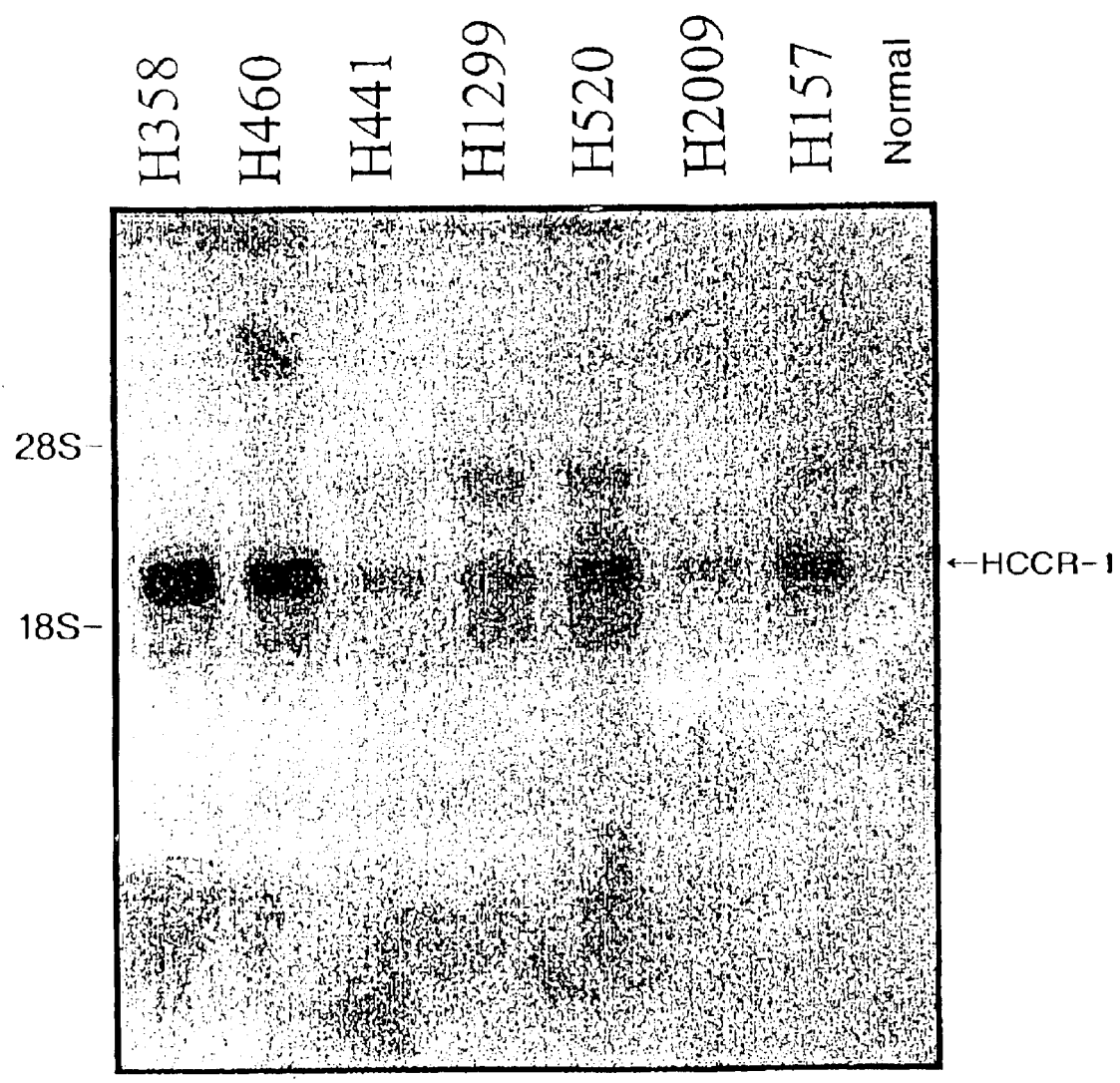
FIG. 4: the results of northern blot analyses for HCCR-1 gene expressed in normal lung tissue and lung cancer cell lines (NCI-H358, NCI-H460, NCI-H441, NCI-H1299, NCI-H520, NCI-H2009, and NCI-H157)

FIG. 4 shows the results of northern blot analyses for HCCR-1 gene expressed in normal lung tissues and seven lung cancer cell lines, i.e., H358(ATCC NCI-H358), H460 (ATCC NCI-H460), H441(ATCC NCI-H441), H299(ATCC NCI-H299), H520(ATCC NCI-H520), H2009(ATCC NCI-H2009), and H157(ATCC NCI-H157). As shown in FIG. 4, HCCR-1 transcription level in high level in lung cancer cell lines H358, H460, H1299, H520, and H1157, but not detectable in the normal lung tissues.

Figure 5A:
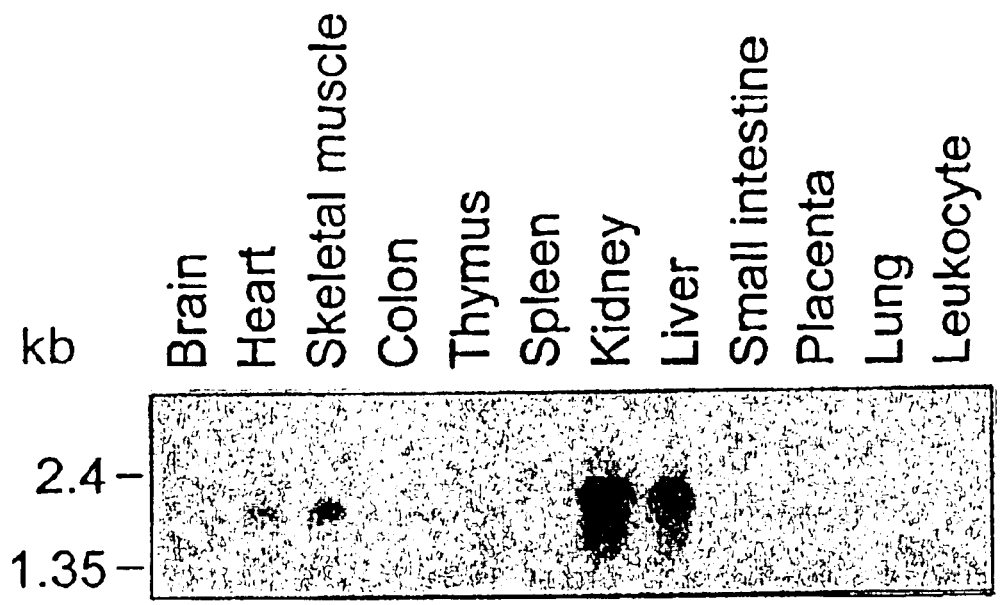
FIG. 5A: the results of northern blot analyses for HCCR-1 gene expressed in normal human 12-lane multiple tissues.
Figure 5B:
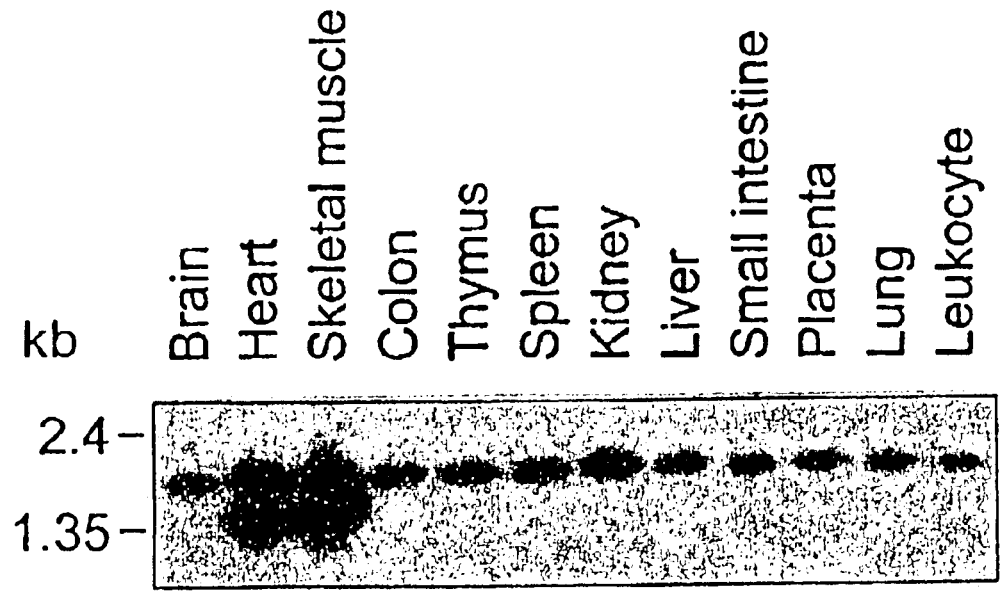
FIG. 5B: the results obtained with the same sample of FIG. 5A hybridized with β-actin.

FIG. 5A shows the results of northern blot analyses for HCCR-1 gene expressed in normal human 12-lane multiple tissues; brain, heart, skeletal muscle, colon, thymus, spleen, kidney, liver, small intestine, placenta, lung and leukocyte tissues(Clontech). FIG. 5B shows the results obtained with the same samples hybridized with a β-actin probe to confirm mRNA integrity. As can be seen in FIG. 5A, HCCR-1 mRNA (~2.1 kb) is weakly present or absent in many normal tissues, but the level of expression was high in normal kidney tissue.

Figure 6A:
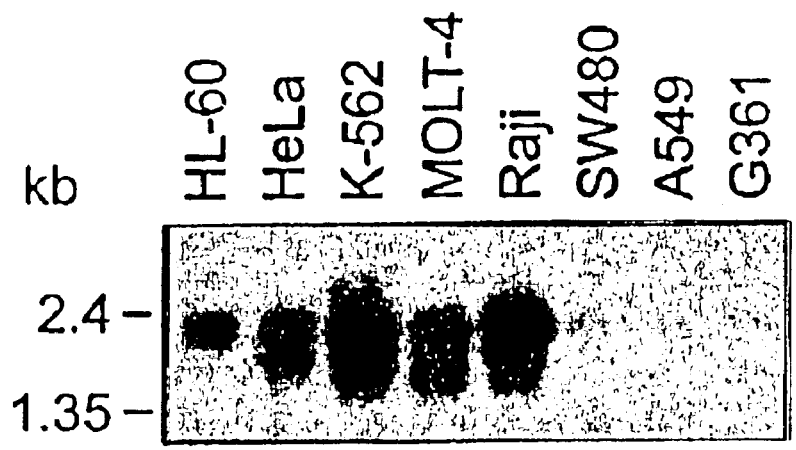
FIG. 6A: the results of northern blot analyses for HCCR-1 gene expressed in human cancer cell lines.
Figure 6B:
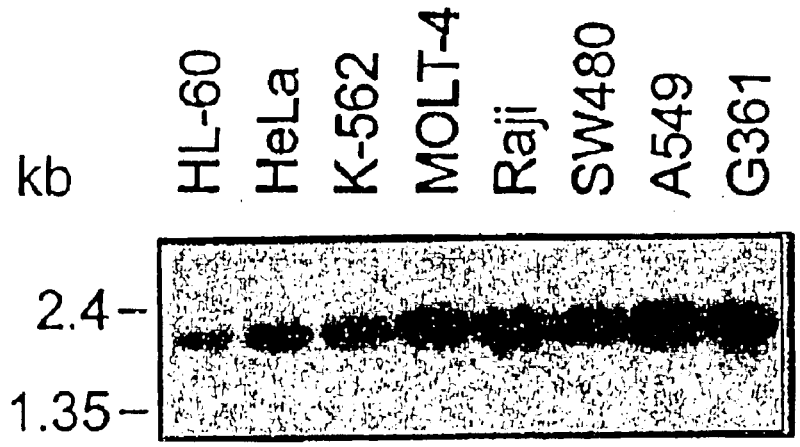
FIG. 6B: the results obtained with the same sample of FIG. 6A hybridized with β-actin.

FIG. 6A shows the results of northern blot analyses for HCCR-1 gene expressed in human cancer cell lines; HL-60, HeLa, K-562, MOLT-4, Raji, SW480, A549 and G361 (Clontech). FIG. 6B shows the results obtained with the same samples hybridized with a β-actin probe to confirm mRNA integrity. As can be seen in FIG. 6A, HCCR-1 is transcribed at a high level in the human leukaemia and lymphoma cell lines such as chronic myelogenous leukaemia K-562, Burkitt's lymphoma Raji, lymphoblastic leukaemia MOLT-4 and promyelocytic leukaemia HL-60 as well as HeLa cells.

K-562, MOLT-4 and HL-60, in particular, show higher transcription levels as compared with normal leukocyte by factors of approximately 190, 90 and 70, respectively. HCCR-1 expression levels in colorectal cancer SW480, lung cancer A549 and melanoma G361 cell lines are lower than those of leukemia and lymphoma.

Figure 7A:
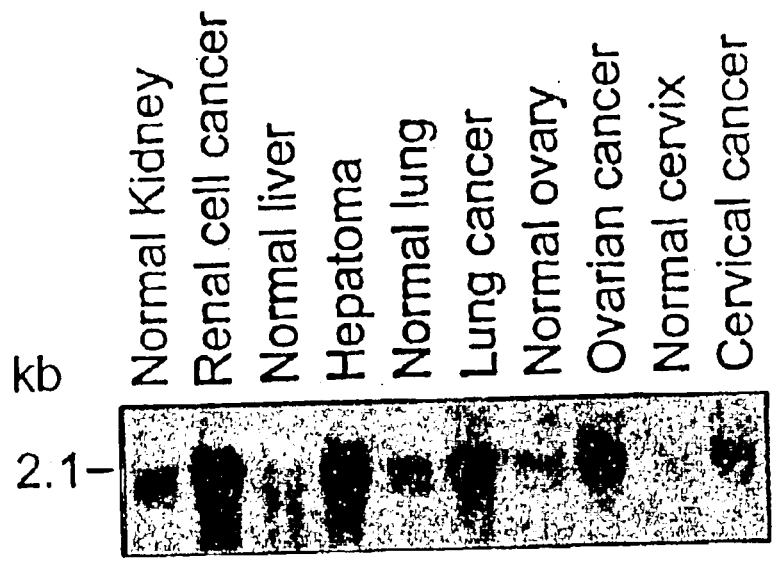
FIG. 7A: the results of northern blot analyses for HCCR-1 gene expressed in human tumor tissues and their normal counterparts.
Figure 7B:
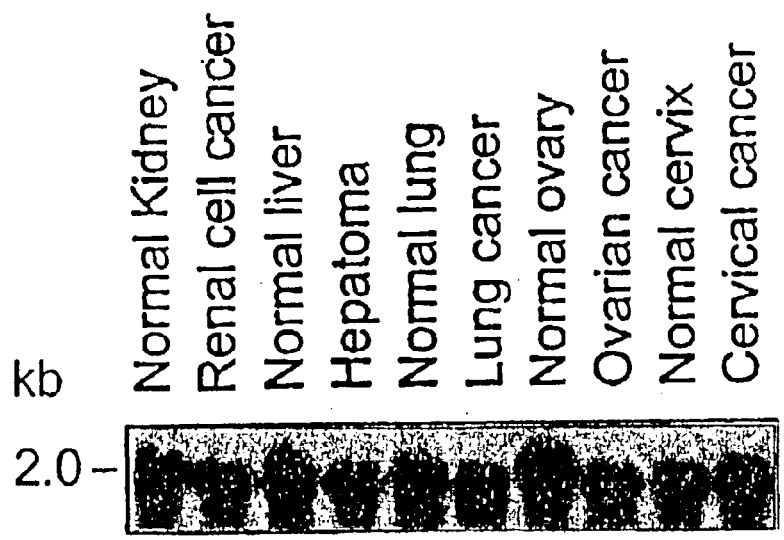
FIG. 7B: the results obtained with the same sample of FIG. 7A hybridized with β-actin.

Further, northern blotting analyses of the human kidney, liver, lung, ovary and cervix tumor tissues and their normal counterparts were carried out. As shown in FIG. 7A, HCCR-1 was transcribed at a high level in the human cancer cells, while the expression of HCCR-1 gene is barely observable in the normal cells. FIG. 7B shows the results obtained with the same samples hybridized with β-actin probe to confirm mRNA ingegrity.

EXAMPLE 8

Micrograph of In Situ Hybridized Human Cervical Cancer Tissues

For in situ hybridization, human cervical cancer tissue was fixed in periodate-lysine-paraformaldehyde, embedded in a wax according to the procedure described by Ahn et al.(*Am. J. Physiol.* 265, F792–F801 (1993)) and sectioned(5 μm). A full-length HCCR-1 cDNA fragment was used to synthesize a digoxigenin-labelled RNA probe. RNA in situ hybridization was carried out with the anti-sense RNA probe which was prepared using a DIG RNA Labelling Kit (Boeringer Mannheim). The sense RNA probe was used as a negative control.

Figure 8:
FIG. 8: a micrograph illustrating representative characteristics of in situ hybridized human cervical cancer tissues.

FIG. 8 shows a micrograph illustrating representative characteristics of in situ hybridized human cervical cancer tissues. As can be seen in FIG. 8, the in situ hybridized cervical cancer tissues are con firm ed to contain a high-level of HCCR-1 gene. No staining was detected in the surrounding normal fibrous tissues.

EXAMPLE 9

Construction of Expression Vectors and Transformation of Cells

Step 9-1: Preparation of a Vector Containing HCCR-1

An expression vector containing the coding region of HCCR-1 was constructed as follows.

First, the entire HCCR-1 cDNA obtained in Example 6 was inserted into the SalI restriction site of a prokaryotic expression vector, pCEV-LAC(see Miki, T. et al., Gene, 83: 137–146 (1989)). Then, the SalI fragment was isolated from the pCEV-LAC/HCCR-1 vector.

Then, pcDNA3 (Invitrogen) was digested with XhoI to make a compatible end with SalI. The SalI fragment containing the full length HCCR-1 coding sequence was inserted into the XhoI-digested pcDNA3. Lipofectamine (Gibco BRL) was used to introduce the resulting pcDNA3/HCCR-1 expression vector into NIH/3T3 cells(ACTC CRL, 1658, USA), followed by selection in a medium supplemented with G418 (Gibco). The resulting NIH/3T3 cells transfected with HCCR-1 was designated "HCCR-1 cells". Another population of NIH/3T3 cells containing pcDNA3 alone was prepared as a control and designated "pcDNA3 cells".

Step 9-2: NIH/3T3 Fibroblast Cells Transfected with the HCCR-1 Protooncogene

Figure 9:
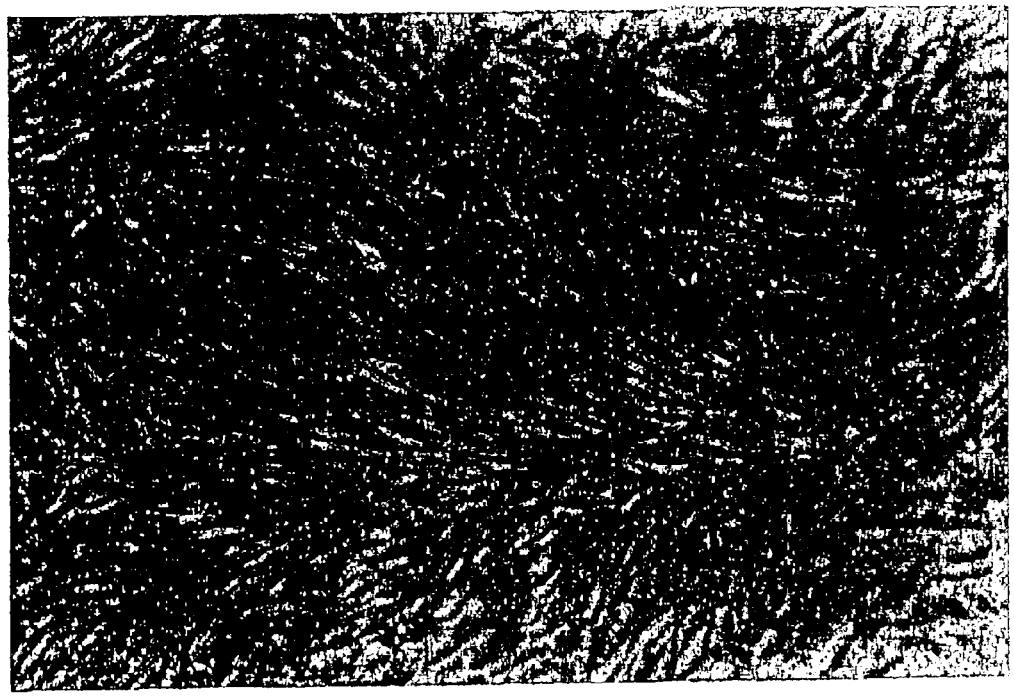
FIG. 9: a phase-contrast feature of monolayer-cultured wild type NIH/3T3 cells.
Figure 10:
FIG. 10: a phase-contrast feature of monolayer-cultured HCCR-1 cells.

The wild type normal NIH/3T3 cell, a differentiated fibroblast cell line, is a spindle shaped cell having a long slender nucleus and a scanty amount of cytoplasm as shown in FIG. 9. When HCCR-1 was expressed in ts the NIH/3T3 expressing HCCR-1(HCCR-1 cells) obtained in Step 9-1, the cell shape changes into a polygonal form with an ovoid nucleus and plump cytoplasm, as shown in FIG. 10.

Figure 11:
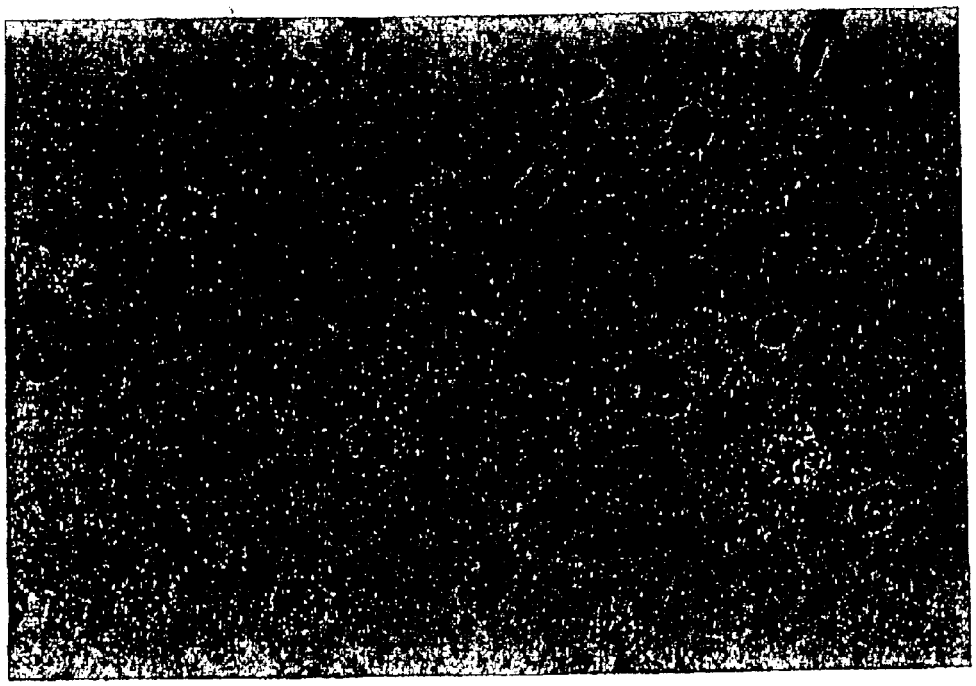
FIG. 11: hematoxylin-eosin staining of monolayer-cultured HCCR-1 cells.

Monolayer cultured HCCR-1-transfected NIH/3T3 cells which is stained with hematoxylin-eosin, exhibit nuclear pleiomorphism, distinct nucleoli, granular chromatin patterns, tumor giant cells and atypical mitotic figures as shown in FIG. 11.

For transmission electron microscopy(TEM), the cells and tissues were fixed with 2.5% glutaraldehyde in a phosphate buffer (pH 7.4). They were then postfixed with a 2% osmium tetroxide. Specimens were dehydrated in a graded series of ethanols and embedded in Epon 812. Ultrathin sections thereof were stained with uranyl acetate and lead citrate, and photographed by TEM(JEOL 1,200 EX, Tokyo, Japan).

Figure 12:
FIG. 12: a transmission electron micrograph illustrating representative characteristics of cultured HCCR-1 cells.

The TEM picture shown in FIG. 12 reveals that cultured tumour cells have microvilli and well-developed organelles (inset). As can be seen in FIG. 12, the HCCR-1 cell has microvilli on the cell surface, lobulated nucleus with prominent nucleoli and well-developed rough endoplasmic reticula(rER) and Golgi complexes (circle). In FIG. 12, the scale bar corresponds to 3 μm. In higher magnification of the area indicated by circle (inset), the scale bar corresponds to 1 μm.

EXAMPLE 10

Tumorigenicity and Metastasis of HCCR-1 Protooncogene in Animal

To analyze tumourigenicity, $5 \times 10^6$ HCCR-1 cells were injected subcutaneously into the posterior lateral aspect of the trunk of 9 mice (5-week-old athymic nu/nu on BALB/c background). Nude mice were sacrificed when the subcutaneous tumors reached 1.5–2.5 cm in diameter.

Figure 13:
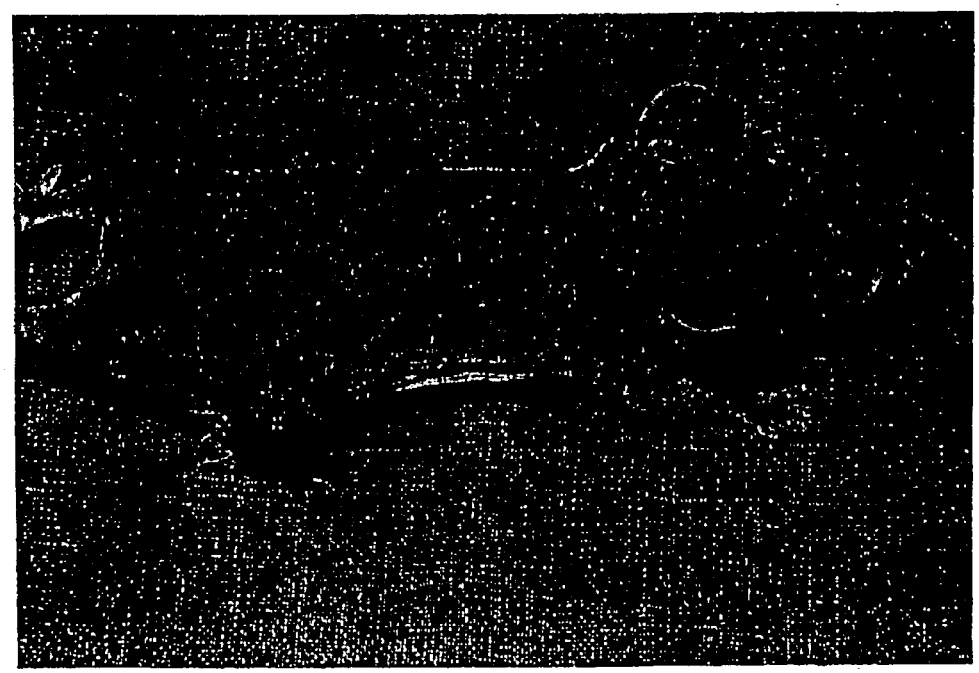
FIG. 13: tumorigenicity of HCCR-1 cells in nude mouse.

All 9 mice injected with HCCR-1 cells showed palpable tumors after 21 days as shown in FIG. 13.

Figure 14:
FIG. 14: hematoxylin-eosin staining of subcutaneous tumour nodules is taken from nude mice.

Nude mice bearing HCCR-1 allografts display characteristics of an epithelial carcinoma. FIG. 14 shows hematoxylin-eosin staining of subcutaneous tumor nodules taken from the nude mice. The sections of the tumour nodules revealed typical epithelial cell nests separated by fibrous stroma.

EXAMPLE 11

Figure 15:
FIG. 15: transmission electron micrographs illustrating representative characteristics of nude mice-derived subcutaneous tumor tissue.

Electron Microscopy of HCCR-1 Protooncogene— induced Tumor Tissue and Establishment of New Cancer Cell Line Tumor tissues taken from the tumor nodules formed on the nude mouse of Example 10 were examined with an electron microscope, which revealed that tumor nodules showed well-developed organelles and tumour cells are connected by desmosomes(FIG. 15). As shown in FIG. 15, the tumor tissue consists of tightly adhered cells with intercellular junction (circle). In FIG. 15, the scale bar corresponds to 3 μm. In higher magnification of the area indicated by circle illustrating desmosome (inset), the scale bar corresponds to 0.5 μm.

Figure 16:
FIG. 16: phase-contrast features of monolayer-cultured nude mice-derived HCCR-1N cells.

The cells obtained from the above tumour tissue was cultured in a conventional manner using 20% fetal bovine serum and the cultured cells were designated HCCR-1N cells which have cytological features similar to HCCR-1 cells in vitro as shown in FIG. 16.

EXAMPLE 12

Determination of Size of Protein Expressed After the Transfection of *E. coli* with HCCR-1 Protooncogene A portion of HCCR-1 protooncogene corresponding to nucleotide Nos. 123–473 and predicted amino acid Nos. 39–155 was inserted into the multiple cloning site of pET-32b(+) vector(Novagen) and the resulting pET-32b(+)/HCCR-1 vector was transfected into *E. coli* BL21(ATCC 47092). The transfected *E. coli* was incubated using an LB broth medium in a rotary shaking incubator, diluted by 1/100, and incubated for 3 hours. 1 mM isopropyl β-D-thiogalacto-pyranoside(IPTG, Sigma) was added thereto to induce the protein synthesis.

Figure 17:
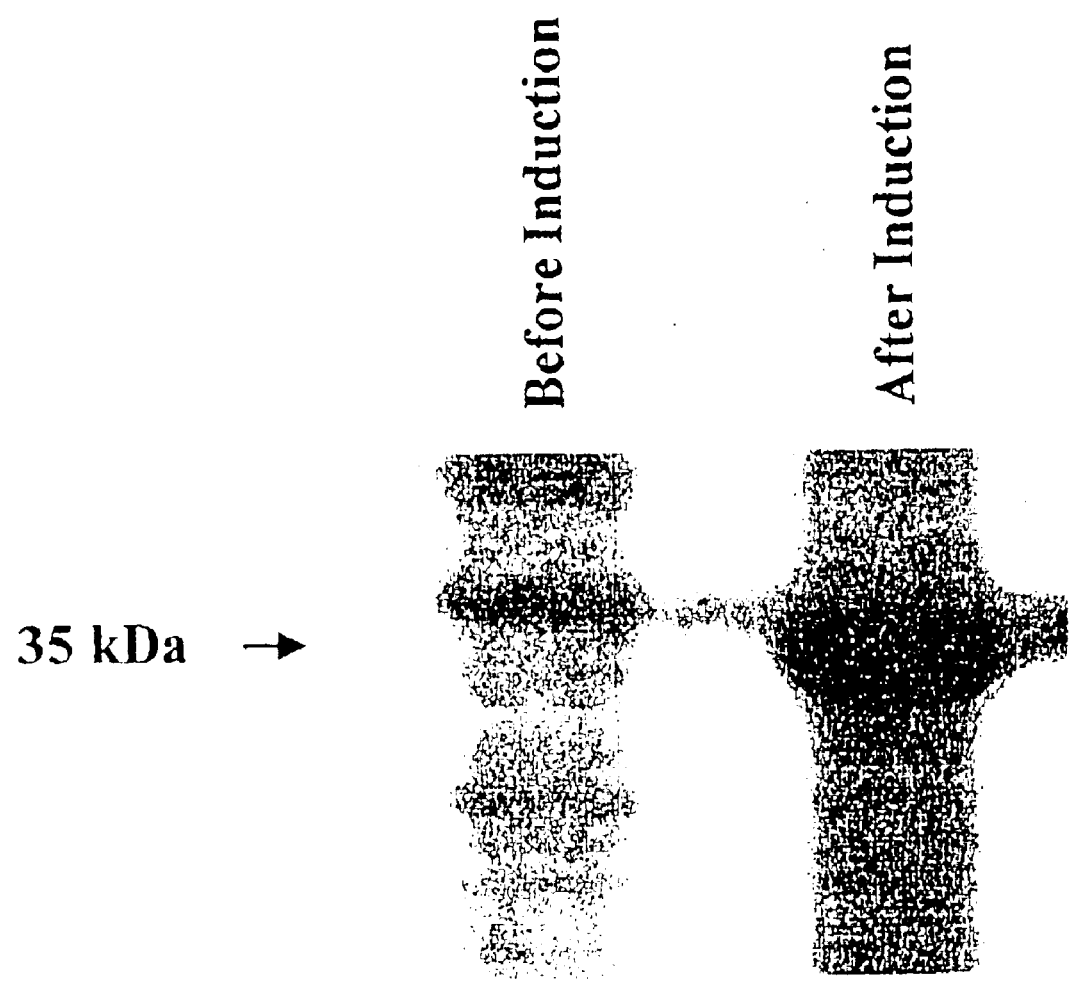
FIG. 17: sodium dodecyl sulfate (SDS)-PAGE results showing protein expression patterns before and after the IPTG induction.

The *E. coli* cells in the culture were disrupted by sonication and subjected to gel electrophoresis using 12% sodium dodecyl sulfate(SDS) before and after the IPTG induction. FIG. 17 shows the SDS-PAGE results which exhibit a protein expression pattern of the *E. coli* BL21 strain transfected with pET-32b(+)/HCCR-1 vector. After the IPTG induction, a significant protein band was observed at about 35 kDa. This 35 kDa fused protein contained an about 20 kDa TrixTag thioredoxin protein expressed a the gene in pET-32b(+) vector.

EXAMPLE 13

Production of Antibody

The 35 kDa fused protein isolated from the *E. coli* BL21 strain transfected with pET-32b(+)/HCCR-1 vector in Example 12 was purified by using a His-Bind Kit (Novagen). Immunoblotting of the purified peptide confirmed the presence of a major amount of a 35 kDa protein.

Then, two 6-seek old Sprague-Dawley rats each weighing about 150 g were each subcutaneously immunized with 1 mg of the peptide thus obtained, weekly for 3 times. Blood samples were obtained from the immunized rats and centrifuged to obtain a polyclonal serum. The anti-HCCR-1 activity of the polyclonal serum was determined and confirmed by enzyme-linked immunosorbent assay(1:10,000)

EXAMPLE 14

Immunoblot Confirming Antibody Specificity

Figure 18:
FIG. 18: the result of western blotting analysis of NIH/3T3 cells without transfection(wild type), NIH/3T3 transfected with pcDNA3 vector alone(pcDNA3) and HCCR-1 cells.
Figure 19:
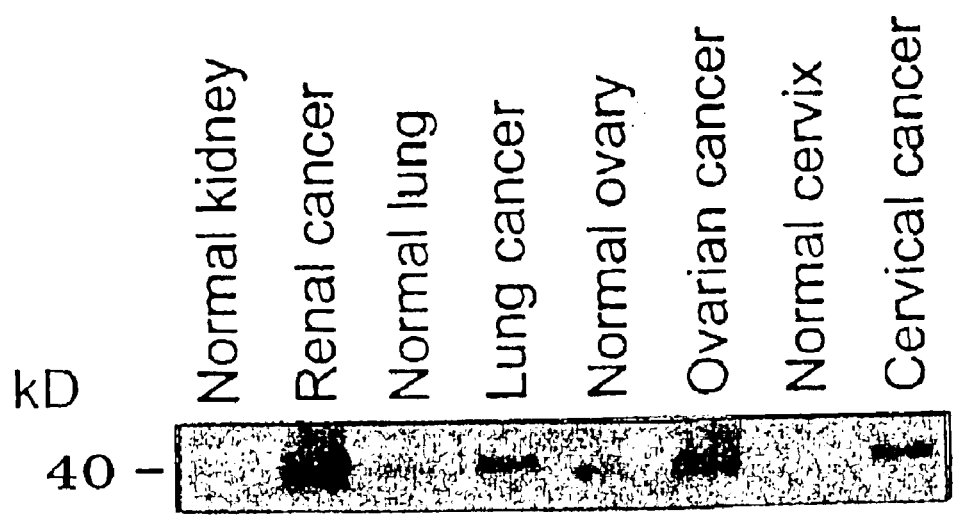
FIG. 19: the result of western blotting analysis of human tumour tissues of kidney, lung, ovary and cervix and their normal counterparts.

For western blot analysis, those cells identified in FIGS. 18 and 19 were harvested and lysed in a Laemmli sample buffer in accordance with the method described by Laemmli (*Nature* 227: 680–685 (1970)). The cellular proteins were separated by 10% SDS-PAGE and then electroblotted onto nitrocellulose membranes. The membranes were incubated with the rat polyclonal anti-HCCR-1 serum prepared in Example 13 for 16 h. After washing, the membranes were incubated with a blocking solution containing 1:1,000 dilution of peroxidase-conjugated goat anti-rat immunoglobulin (Jackson ImmunoResearch) as a secondary antibody. Proteins were revealed by an ECL-Western blot detection kit (Amersham).

As shown in FIG. 18, HCCR-1 protein is overexpressed in HCCR-1 cells, while only faint bands are observed for the wild type and cells transfected with the vector alone (pcDNA3). This result illustrates the specificity of the anti-HCCR-1 antibodies in the polyclonal serum.

Further, the HCCR-1 antibody in the polyclonal serum recognized approximately 40 kDa protein in human protein extracts from different tissues. As shown in FIG. 19, human tumor tissues including carcinomas of the kidney, lung, ovary and cervix showed increased HCCR-1 protein expression when compared with their normal counterparts.

EXAMPLE 15

Immunohistochemistry

The tumor nodules formed on the nude mouse of Example 9 were incubated with anti-vimentin, anti-keratin, anti-EMA (epithelial membrane antigen) antibodies (DAKO) and polyclonal antibody raised against HCCR-1, respectively. Then, immunohistochemistry was carried out on 5 μm-cryosections of the incubated tumor nodules.

Figure 20:
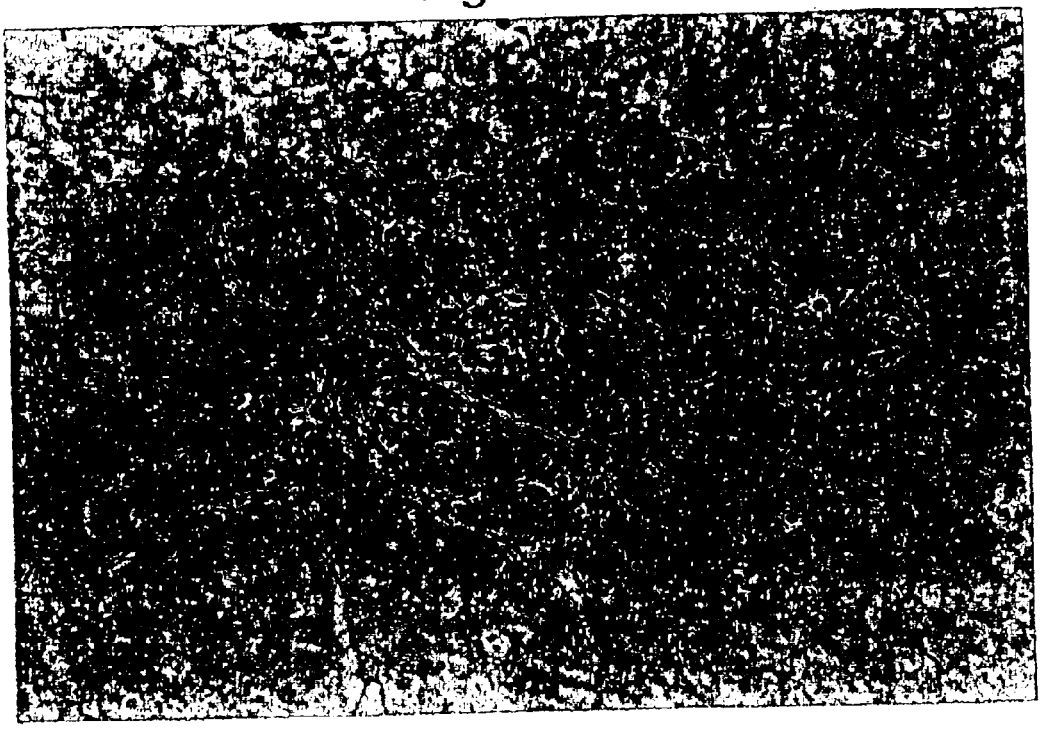
FIG. 20: the immunohistochemical study of HCCR-1-transfected NIH/3T3 cells against reticulin fibers (×250)

Binding of primary antibody was visualized by biotinylated secondary antibody, avidin, biotinylated horseradish peroxidase and AEC(Aminoethyl Carbaxzole Substrate Kit) as the chromogen(HISTOSTAIN-BULK KITS, Zymed). The immunohistochemical study revealed that HCCR-1 transfection into NIH/3T3 cells caused the conversion of the cell nature from mesenchymal to epithelial. The cell nests were enveloped by reticulin fibers as shown in FIG. 20.

Figure 21:
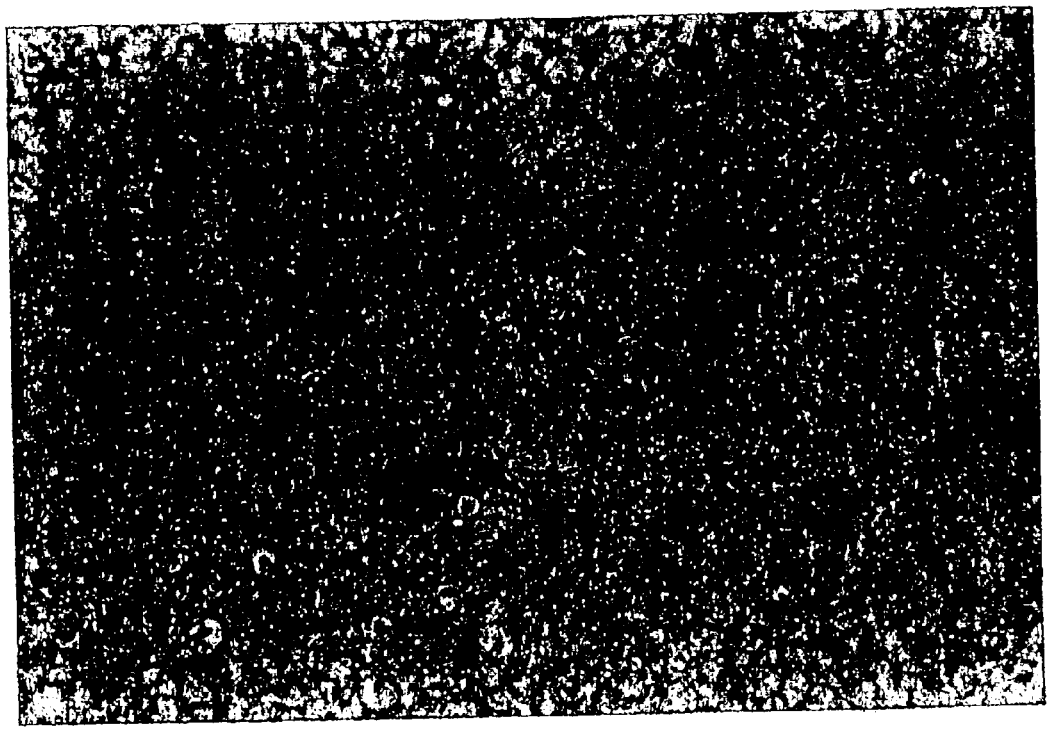
FIG. 21: the expression of epithelial marker, keratin in HCCR-1-transfected NIH/3T3 cells (×250)
Figure 22:
FIG. 22: the expression of epithelial membrane antigen in HCCR-1-transfected NIH/3T3 cells (×250)
Figure 23:
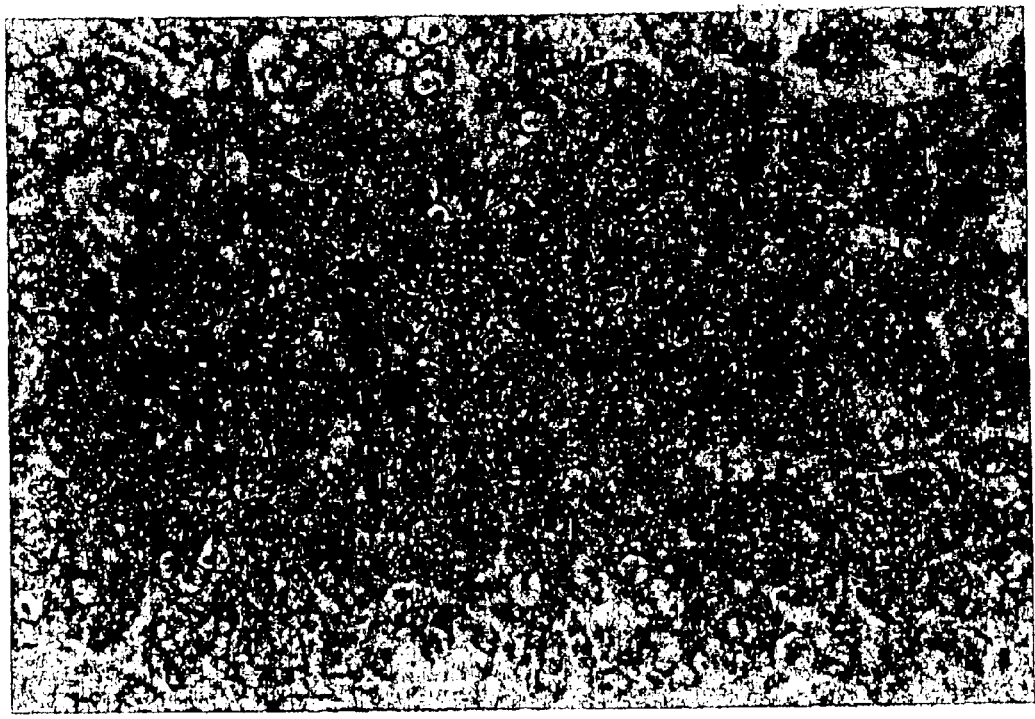
FIG. 23: the expression of mesenchymal marker, vimentin in HCCR-1-transfected NIH/3T3 cells (×250)

The cells showed coexpression of epithelial markers, such as keratin(FIG. 21) and epithelial membrane antigen (FIG. 22) and of the mesenchymal marker, vimentin(FIG. 23).

EXAMPLE 16

Protein Kinase C and Telomerase Activity Assays

To ensure that HCCR-1 modulates the protein kinase C(PKC) activity in cells, PKC assay was performed using wild-type NIH/3T3 cells, pcDNA3-containing NIH/3T3 cells and HCCR-1-transfected NIH/3T3 cells prepared in Step 9-1 of Example 9.

PKC activity was measured using the SignaTECT™Protein Kinase C Assay System (Promega) according to the manufacturer's instructions. PKC activity was defined as the difference of the amounts of PKC incorporated into substrate per minute in the absence and presence of phospholipids. Each value is the means±s.d. of three independent experiments.

Figure 24:
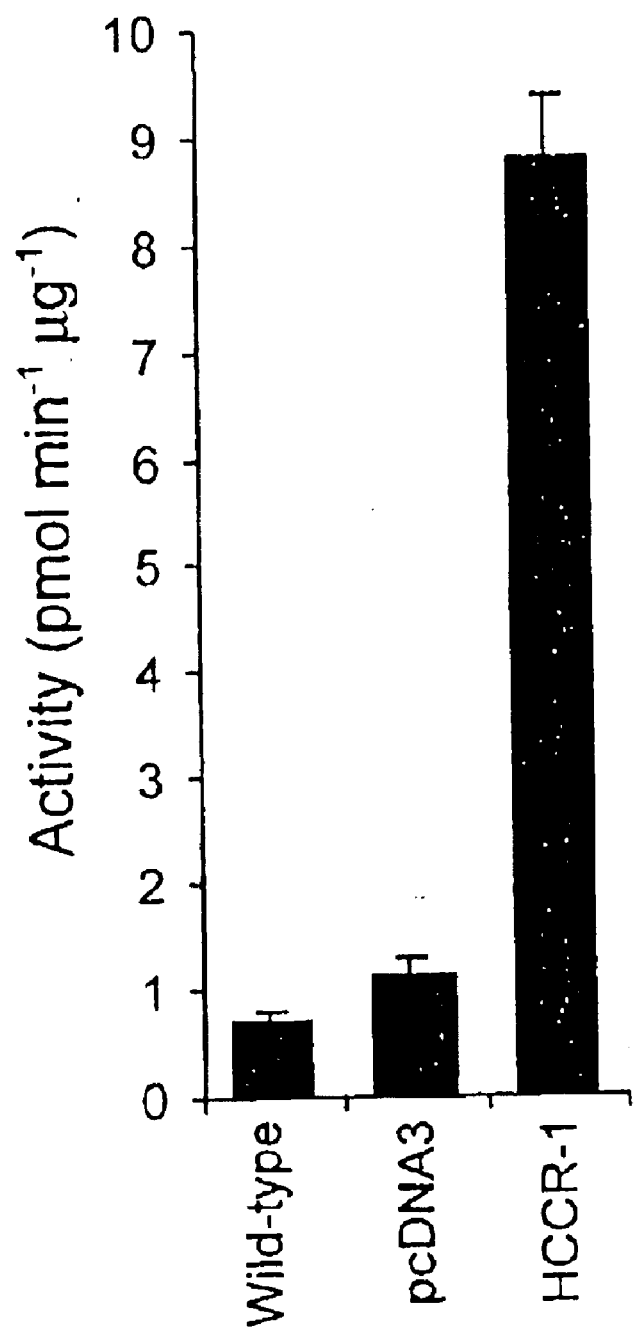
FIG. 24: the PKC activities in NIH/3T3 cells without transfection(wild-type), NIH/3T3 transfected with pcDNA3 vector alone(pcDNA3) and NIH/3T3 transfected with HCCR-1 protooncogene (HCCR-1 cells)

The result in FIG. 24 shows that the PKC activity of HCCR-1-transfected NIH/3T3 cells is about 10-fold higher than the wild-type.

To explain the tumorigenesis of HCCR-1, telomerase activities in wild-type NIH/3T3 cells, pcDNA3-containing NIH/3T3 cells and HCCR-1-transfected NIH/3T3 cells prepared in Step 9-1 of Example 9 were measured using the telomerase PCR-ELISA kit (Boehringer Mannheim) according to the manufacturer's instructions. Human telomerase-positive immortalized human kidney cells (293 cells) provided in the kit were used as a positive control.

Used as a negative control was the 293 cells pretreated with RNase (+RNase). Assays were performed with an extract amount equivalent to $1 \times 10^3$ cells.

Figure 25:
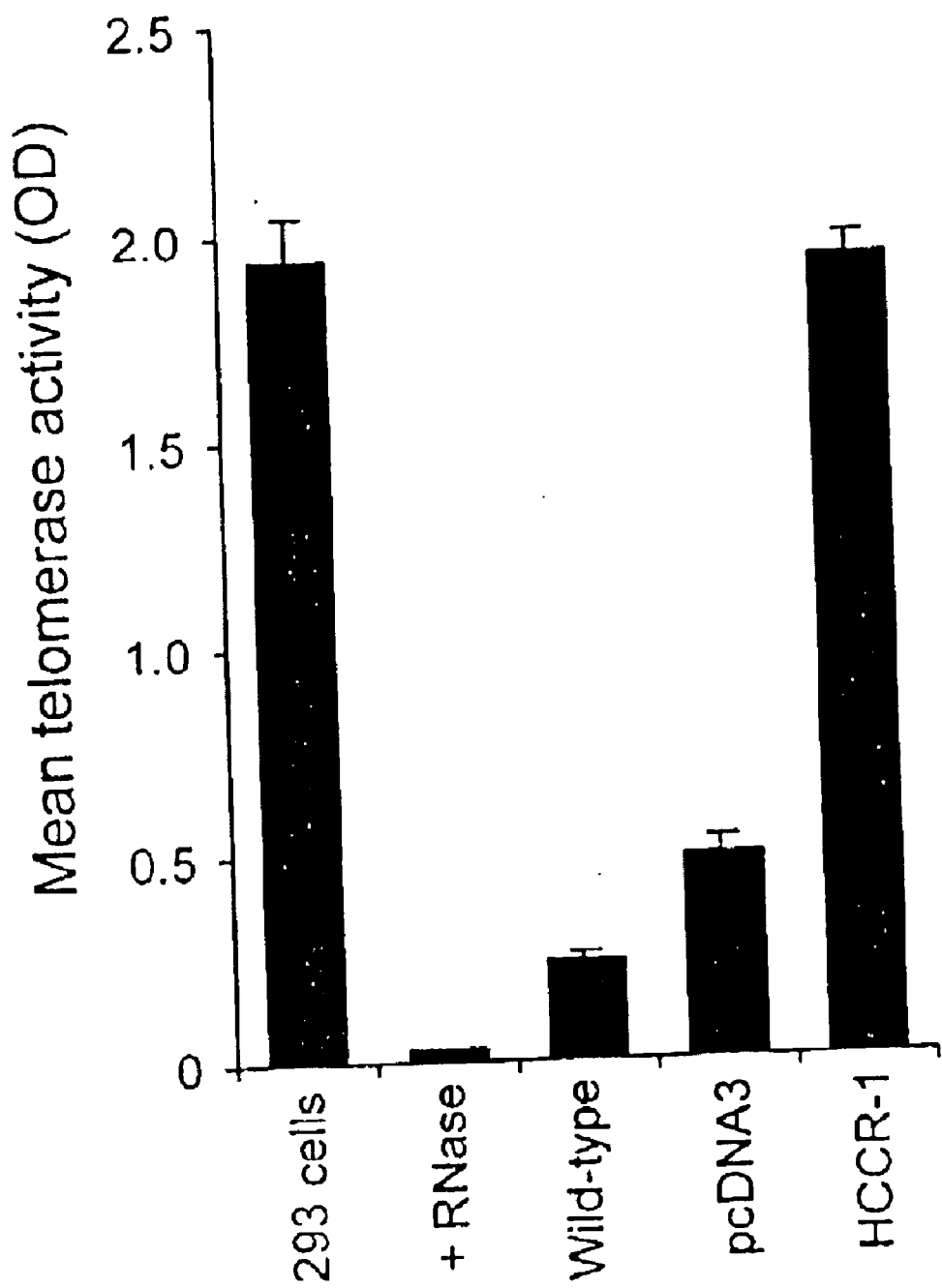
FIG. 25: the telomerase activities in 293 cells, +RNase, NIH/3T3 cells without transfection(wild-type), NIH/3T3 transfected with pcDNA3 vector alone(pcDNA3) and NIH/3T3 transfected with HCCR-1 protooncogene(HCCR-1 cells)

Results in FIG. 25 show the average mean optical density (OD) values from four separate experiments (means±s.d.). Consistent with the previous study (Holt, S. E., Wright, W. E. and Shay J. W. *Mol. Cell Biol.* 16, 2932–2939 (1996), wild-type NIH/3T3 cells showed detectable telomerase activity. HCCR-1 gene transfection raised the telomerase activity by a factor of about 7 as compared with the wild-type cells. The high telomerase activity of the 293 cells was nullified by pretreatment with RNase.

EXAMPLE 17

Cell Cycle Experiments

Wild-type and HCCR-1-transfected NIH/3T3 cells cultured in a DMEM medium at mid-log phase were growth arrested by incubation in a DMEM medium containing 0.5% bovine calf serum for 36 h. Cells to be analyzed for the DNA content were harvested following trypsinization, and fixed in 70% ethanol. Fixed cells were then stained with propidium iodide as described by Hedley(*Flow Cytometry, DNA Analysis from Paraffin-embedded Blocks*; Darzynkiewicz, Z. & Crissman, H. A. eds., Academic Press, San Diego, 1990).

First, 50 μg/ml of a propidium iodide staining solution (Sigma) and 100 units per ml of RNase A (Boerhinger Mannheim) were added to $2 \times 10^6$ cells. After incubation for 1 h, the cellular DNA content was determined by fluorescence analysis at 488 nm using a FACS Caliber (Becton Dickinson). A minimum of $1 \times 10^4$ cells per sample was analyzed with Modfit 5.2 software.

In order to study whether there was an alteration in the growth properties of HCCR-1-transfected NIH/3T3 cells, cell cycle profiles were examined. The cell contents of the wild type NIH/3T3 cells and HCCR-1 transfected NIH/3T3 cells(mid-log phase) in $G_0/G_1$, S, $G_2/M$ phases were measured and the results are shown in Table I.

TABLE I

|  | Wild Type | | | HCCR-1 Cell | | |
| --- | --- | --- | --- | --- | --- | --- |
|  | $G_0/G_1$ | S | $G_2/M$ | $G_0/G_1$ | S | $G_2/M$ |
| Cell Content (%) | 55.7 | 20.6 | 24 | 46.6 | 31.5 | 22.4 |

As can be seen from Table I, the percentage of wild-type and HCCR-1 transfected NIH/3T3 cells in the S-phase was 20.6% and 31.5%, respectively (mid-log phase). These results suggest that there was a signigicant shift of the cell pipulation out of the $G_0/G_1$-phase into the S-phase in HCCR-1 transfected NIH/3T3 cells.

To assess the serum-dependent cell cycle progression, cells were cultured in 0.5% bovine calf serum for 36 h. After incubation, cells were released with 20% bovine calf serum and harvested at indicated times. The cell contents of wild type NIH13T3 cells and HCCR-1 transfected NIH/3T3 cells in $G_0/G_1$, S, $G_2/M$ phases at indicated times were measured and the results are shown in Table II.

TABLE II

|  | Cell Content (%) | | | | | |
| --- | --- | --- | --- | --- | --- | --- |
|  | Wild Type | | | HCCR-1 Cell | | |
| Time (h) | $G_0/G_1$ | S | $G_2/M$ | $G_0/G_1$ | S | $G_2/M$ |
| 0 | 77 | 8.0 | 14.9 | 70 | 21.8 | 8.7 |
| 12 | 72.2 | 14 | 14.2 | 66.9 | 24.0 | 9.6 |
| 24 | 49.6 | 13.4 | 37.2 | 56.7 | 24.7 | 19.2 |
| 48 | 58.3 | 18.3 | 23.7 | 52.7 | 30.4 | 17.5 |

As can be seen from Table II, few cells remained in the S-phase in wild-type cells measured at 0 h (8%). In contrast, a considerable number of HCCR-1 cells measured at 0 h were still in the S-phase (21.8%), suggesting that constitutive overexpression of HCCR-1 allowed for a relative amount of resistance to serum deprivation-induced $G_0/G_1$ arrest. Following the release of cells from the growth arrest caused by serum-deprivation, there were consistent increases of over 10% in the S-phase populations of HCCR-1 cells as compared to wild-type cells at measured time intervals (12 h, 24 h and 48 h). Therefore, overexpression of HCCR-1 could deregulate cell growth by shortening the $G_0/G_1$-phase and increasing the S-phase population of cells.

EXAMPLE 18

Construction of Anti-sense Oligodeoxinucleotide

Anti-sense and sense phosphorothioate oligodeoxynucleotide(ODNs) targeting the translation starting site of HCCR-1 mRNA were synthesized based on the human HCCR-1 cDNA sequence (GenBank accession number AF195651) by cyanoethylphosphoramidite chemistry on an automated DNA synthesizer (Expedite Nucleic Acid System, Framingham, Mass.).

The sequence of 18-mer HCCR-1 anti-sense ODN was 5'-CCTGGACATTTGTCACC-3' (SEQ ID NO: 3; corresponding to nucleotide Nos. 66 to 83 of SEQ ID NO:1). The corresponding sense sequence, 5'-GGTGACAAAATGTCCAGG-3'(SEQ ID NO: 4), and missense sequence, 5'-CGCGGATATTTCCTCACC-3'(SEQ ID NO: 5) were used as conltrolis.

EXAMPLE 19

Cancer Gene Therapy Using HCCR-1 Antisense ODN

Step 19-1: Inhibition of Gene Expression

Exponentially growing $2 \times 10^5$ H-358 lung carcinoma cells (ATCC CRL-5807) were detached by trypsin-EDTA and seeded in a 24-well plate. Lipofectamine (Gibco BRL) was used for oligodeoxynucleotide(ODN) treatment. Lipofectamine (5 μl/ml medium) was incubated with an appropriate amount of ODN to achieve a final concentration of 100 nM ODN, in the cell suspension for 30 minutes at room temperature. Then 1,000 μl portions of the mixture were added directly to the cells on the 24-well plates and incubated for 1, 2, 3, 5 and 7 days, respectively. There was no cytotoxicity of the transfection reagent as controlled by trypan blue dye exclusion assay.

To observe the inhibitory effect of HCCR-1 anti-sense ODN, the cultured lung carcinoma cells were treated with 100 nM each of sense, missense and anti-sense ODNs obtained in Example 18, respectively. Inhibition of HCCR-1 expression in anti-sense ODN-treated lung carcinoma cells was demonstrated by reverse transcription-polymerase chain reaction (RT-PCR). The sequences of oligonucleotide primers used for RT-PCR, synthesized according to the coding region of HCCR-1 CDNA were as follows: forward, 5'-GGGAGATGGAGCATTTGAGA-3' (SEQ ID NO:6, corresponding to nucleotides Nos. 376–395 of SEQ ID NO:1) and reverse, 5'-GCTTCCGGAAAGCATGATAG-3'(SEQ ID NO:7, corresponding to nucleotides 554–573 of SEQ ID NO:1.

Figure 26A:
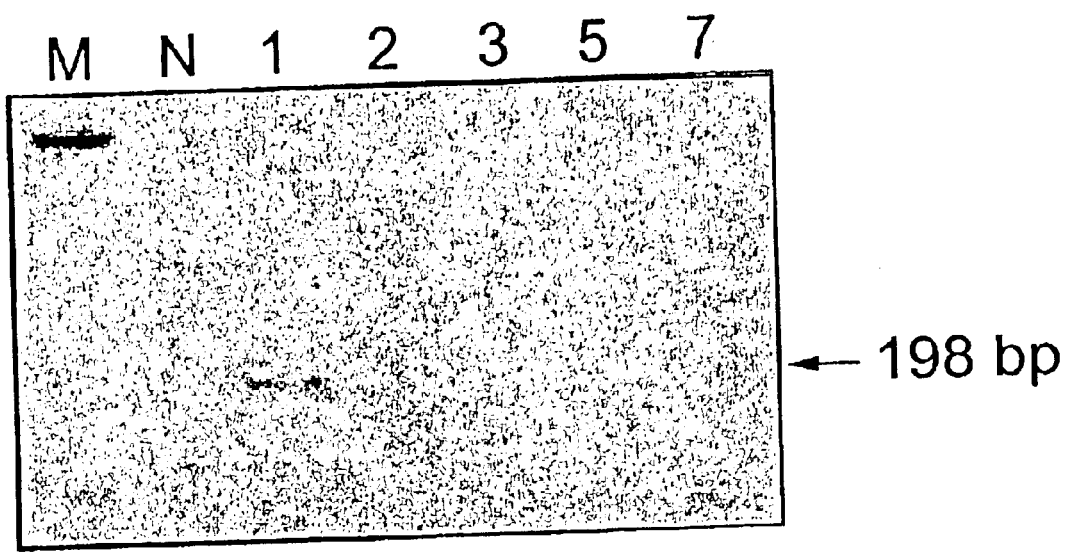
FIG. 26A: the results of RT-PCR amplification of HCCR-1 cDNA in H-358 lung carinoma cell lines treated with anti-sense oligodeoxynucleoties.
Figure 26B:
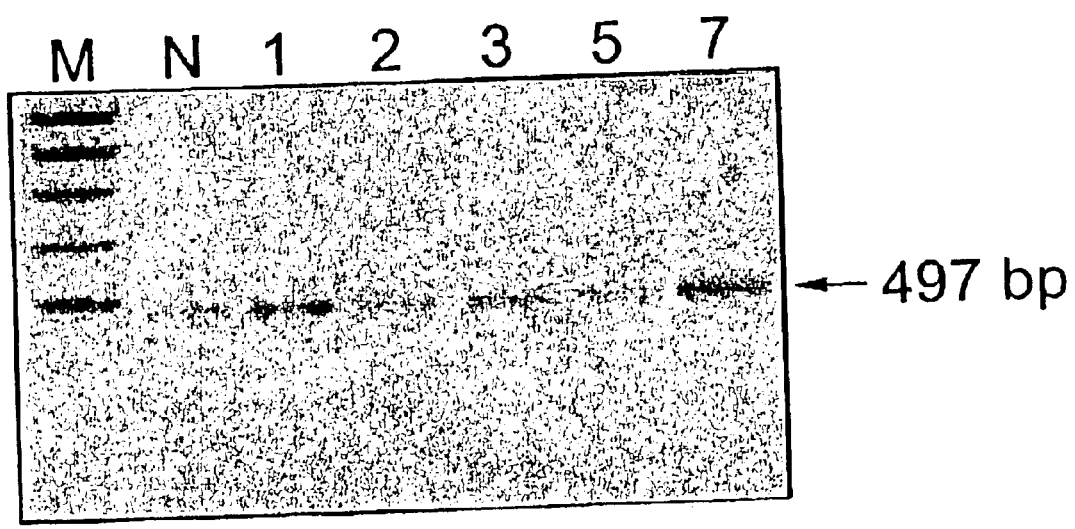
FIG. 26B: the results obtained with the same sample of FIG. 26A hybridized with β-actin.

The dose of anti-sense exerting inhibitory effect was related to the levels of HCCR-1 mRNA expression(FIG. 26A). 497 bp β-actin was used as an internal control to confirm mRNA integrity(FIG. 26B). A negative control(N) contained nuclease-free water instead of RNA template. 1000-bp ladder DNA size marker(M) was also used. As shown in FIG. 26A, the level of 198 bp HCCR-1 RT-PCR product decreased in a time-dependent manner by anti-sense ODN treatment. HCCR-1 gene expression was completely inhibited in cells treated with 100 nM of anti-sense HCCR-1

ODN for 7 days. In contrast, expected 198 bp HCCR-1 RT-PCR product was detected in cells treated with 100 nM of sense or missense HCCR-1 ODN, respectively, and in the untreated parental cells.

These results show that the treatment with 100 nM of anti-sense HCCR-1 ODN completely blocks HCCR-1 gene expressions in lung carcinoma cells.

Step 19-2: Inhibition of Cell Growth

The growth phenotype of H-358 lung cancer cells treated with 100 nM of sense, anti-sense or missense HCCR-1 oligodeoxynucleotide was assessed by growth curve.

In three independent experiments, H-358 lung cancer cells were trypisinized and plated in the presence of 100 nM of sense, anti-sense or missense HCCR-1 ODN obtained in Example 18, and a growth medium(RPMI-1640) containing 100 nM of HCCR-1 ODN was replaced every other day. Cells in triplicate dishes were detached and viable cells were counted every other day using trypan blue dye exclusion.

Figure 27:
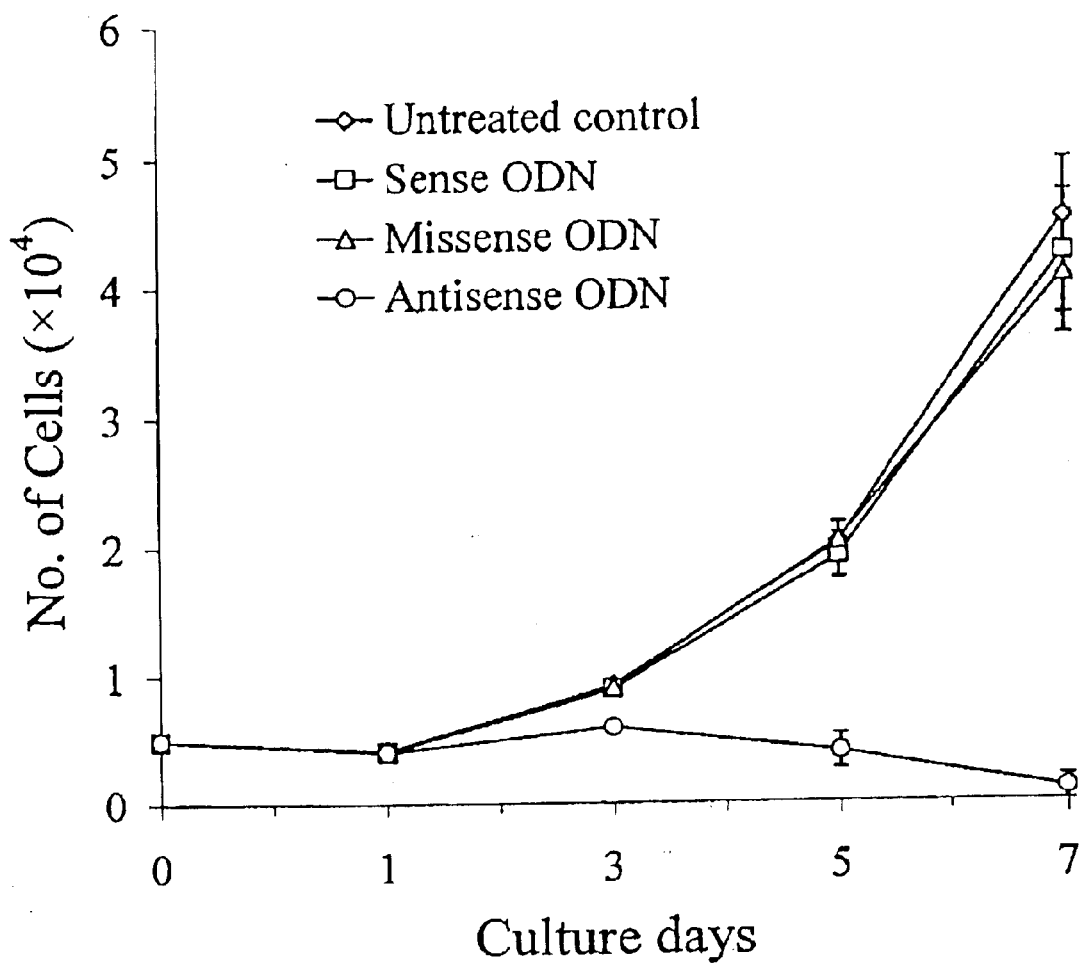
FIG. 27: growth curves of H-358 lung carcinoma cell lines treated with sense, missense or anti-sense HCCR-1 ODN, and untreated parental cells.

As shown in FIG. 27, until 1 day of treatment, there were no discernable differences in cell growth among sense(☐), missense(☐) or anti-5 sense(o) HCCR-1 ODN-treated carcinoma cells. However, after 3 days of HCCR-1 ODN treatment, anti-sense HCCR-1 ODN inhibited lung carcinoma cell growth in a time-dependent manner.

After 7 days exposure to antisense HCCR-1 ODN, the extent of growth inhibition was about 100% for H-358 lung carcinoma cells, while cells exposed to sense or missense HCCR-1 ODN showed growth patterns similar to that of untreated wild-type H-358 cells(control cells,).

EXAMPLE 20

HCCR-1 Gene as a Regulator of Embryonic Kidney Development

Because the acquisition of epithelial properties by the fibroblast-derived HCCR-1 cells mimics the mesenchymnal to epithelial conversion of cells during the organogenesis of the kidney (Giordano, S. et al., *Proc. Natl. Acad. Sci. USA* 90, 649–653 (1993): Tsarfaty, I., et al., *Science* 263, 98–101 (1994)), an experiment was conducted to examine whether HCCR-1 is expressed in a developing kidney.

Total proteins in tissue extracts of fetal 16-, 18- and 20-day rat kidneys, postnatal 1-, 7- and 14-day rat kidneys and adult rat kidney were subjected to SDS-PAGE. HCCR-1 protein in HCCR-1 positive bands were detected by ECL-Western blot detection kit employing rat polyclonal anti-HCCR-1 serum as in Example 14.

Figure 28:
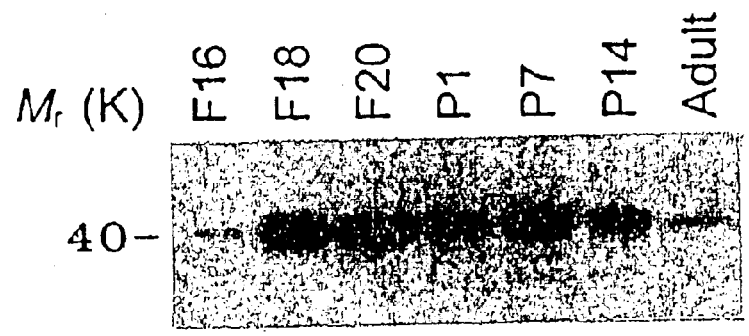
FIG. 28: HCCR- 1 protein expressions in fetal 16-(F16), 18-(F 18), 20-(F20), postnatal 1-(P1), 7-(P7), 14-day(P14) and adult rat kidney tissue extracts.

The result in FIG. 28 demonstrates that HCCR-1 protein having a relative molecular mass of approximately 40,000 ($M_r$~40K) begins to be overexpressed at fetal 18-day remains at a high expression level up to postnatal 14-day, and decreases to a very low level in adult rat kidney. In FIG. 28, F and P denote fetal and postnatal, respectively.

Figure 29:
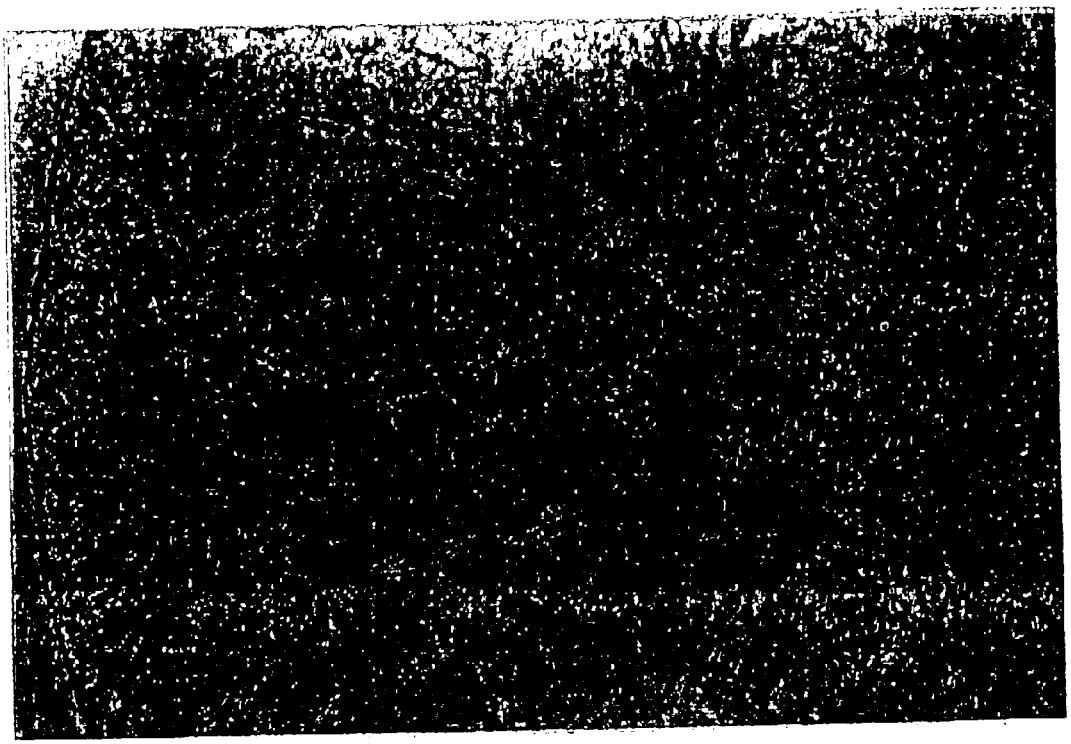
FIG. 29: immunohistochemical staining of 20 day-old fetal rat kidney (x42)

A 20-day-old fetal rat kidney was subjected to an immunohistochemical staining as in Example 15. As revealed in FIG. 29 which shows a stained section of the rat kidney (Magnification, ×42), HCCR-1 antibody stained the collecting ducts only (medulla on the left side), which are derived from the ureteric bud (Saxen, L. *Organogenesis of the kidney*. 88–128 (Cambridge University Press, Cambridge, United Kingdom, 1987); Coles, H. S., et al., *Development* 118, 777–784 (1993)). The developing nephrons in the cortex were not stained (nephrogenic zone on the right side).

Figure 30:
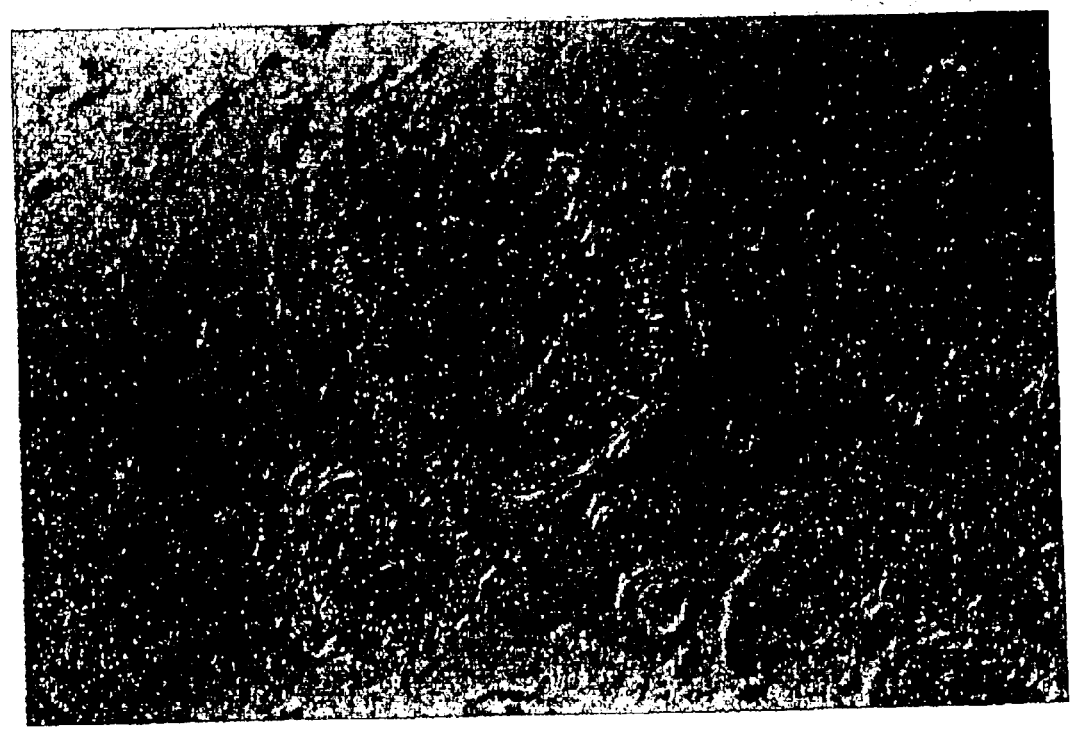
FIG. 30: differential-interference contrast microscopy of 18 day-old fetal rat kidney illustrating HCCR-1 immunostaining in the basolateral plasma membrane of medullary collecting duct (×220).

Further, a 18-day-old fetal rat kidney was subjected to an immunohistochemical staining as in Example 15 and, then, observed under a differential-interference contrast microscope. As shown in FIG. 30, the basolateral plasma membranes of medullary collecting duct were especially reactive to HCCR-1 antibody(Magnification, ×220).

Because nephrogenesis is stimulated by a distinct ureteric signal, diffusion-limited basolateral molecules (Barasch, J., et al., *Am. J. Physiol.* 271, F50–F61 (1996)), which trigger mesenchymal to epithelial conversion, it is presumed that the HCCR-1 product may be a mesenchyme-derived regulatory factor (Barasch, J. et al., *Cell* 99, 377–386 (1999): Barasch, J. et al., *J. Clin. Invest.* 103, 1299–1307 (1999)) that stimulates morphogenesis of epithelia in the kidney developmental process and mediates interactions between mesenchyme and epithelia during neoplastic transformation.

The present specification includes the appended Sequencing Listing of 47 nucleic acid or amino acid sequences. Articles of the patent and scientific periodical literature cited herein are thereby incorporated in their entity by such citation.

While the embodiments of the subject invention have been described and illustrated, it is obvious that various changes and modifications can be made therein without departing from the spirit of the present invention which should be limited only by the scope of the appended claims.

What is claimed is:

1. A human cervical cancer 1 protooncogene having the base sequence of SEQ ID NO:1.

2. A human cervical cancer 1 protooncogene having a base sequence corresponding to base Nos. 9 to 1088 of SEQ ID NO:1.

3. A vector comprising the protooncogene of claim 1.

4. A microorganism transformed with the vector of claim 1.

5. The microorganism of claim 4, which is *E. coli* JM109/HCCR-1(Accession No.: KCTC. 0667BP).

6. A process for preparing the protein having the amino acid sequence of SEQ ID NO: 2 by culturing the microorganism of claim 4.

7. A kit for diagnosis of cancer which comprises the protooncogene of claim 1.

8. An anti-sense gene having a base sequence which is complementary to the sequence of the mRNA transcribed from the protooncogene of claim 1 and being capable of binding the mRNA to inhibit the expression of said protooncogene.

9. The anti-sense gene of claim 8 having the base sequence of SEQ ID NO:3.

10. A process for preparing the protein having the amino acid sequence of SEQ ID NO: 2 by culturing the microorganism of claim 6.

11. A kit for diagnosis of cancer which comprises the protooncogene of claim 2.

12. An anti-sense gene having a base sequence which is complementary to the sequence of the mRNA transcribed from the protooncogene of claim 2 and being capable of binding the mRNA to inhibit the expression of said protooncogene.

13. A vector comprising the protooncogene of claim 2.

14. A microorganism transformed with the vector of claim 13.

15. A process for preparing the protein having the amino acid sequence of SEQ ID NO: 2 by culturing the microorganism of claim 14.

* * * * *